(12) United States Patent
Limaye et al.

(10) Patent No.: US 11,749,393 B2
(45) Date of Patent: Sep. 5, 2023

(54) SYSTEMS, APPARATUSES AND METHODS FOR CAPTURING IMAGES OF MEDICAL CONDITION MANAGEMENT EVENTS AND RELATED EQUIPMENT WITH SMARTPHONE AND RELATED APP THAT PROCESSES IMAGES TO REDUCE MEDICAL ERRORS

(71) Applicant: Becton, Dickinson and Company, Franklin Lakes, NJ (US)

(72) Inventors: Amit Uday Limaye, Wayne, NJ (US); Elaine Tam, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 245 days.

(21) Appl. No.: 16/883,611

(22) Filed: May 26, 2020

(65) Prior Publication Data

US 2020/0381106 A1     Dec. 3, 2020

Related U.S. Application Data

(60) Provisional application No. 62/855,531, filed on May 31, 2019.

(51) Int. Cl.
*G16H 40/20* (2018.01)
*G08B 21/04* (2006.01)
(Continued)

(52) U.S. Cl.
CPC ........... *G16H 20/17* (2018.01); *A61B 5/0002* (2013.01); *A61B 5/01* (2013.01); *A61B 5/021* (2013.01);
(Continued)

(58) Field of Classification Search
CPC ........ G16H 40/20; G16H 30/40; G06V 20/64; G06V 20/00; A61B 5/0002; A61B 5/14551; A61B 5/746; G08B 21/0461
See application file for complete search history.

(56) References Cited

U.S. PATENT DOCUMENTS 5,902,982 A    5/1999   Lappe
10,650,267 B2 *   5/2020   Yoshida ................. G16H 30/40
(Continued)

FOREIGN PATENT DOCUMENTS

WO     2020109888 A1     6/2020

OTHER PUBLICATIONS

International Search Report and Written Opinion dated Aug. 19, 2020, which issued in the corresponding PCT Patent Application No. PCT /US2020/034815.

*Primary Examiner* — Santiago Garcia
(74) *Attorney, Agent, or Firm* — Dickinson Wright PLLC

(57) ABSTRACT

Device(s) with camera and medical event image capture app and method(s) are provided to capture images of medical condition management events involving products with indicia, perform image processing and analysis of captured images to discern product characteristics, artifacts and/or related informatics from indicia and other image elements in the captured image, and perform human machine interaction (HMI) operations or other logical operations that alert a user regarding a selected informatic or request input or otherwise educate the user about an aspect of medical condition management. The medical event image capture app provides any one or more of confirmation of correct or compatible product(s), dose confirmation, and detection of defective product or medication or misuse. The medical event image capture app provides auto-recording of medical event data into patients' electronic records, and assists with healthcare
(Continued)

administration including billing, medical products inventory management and reordering, care plan compliance, and clinical effectiveness.

20 Claims, 16 Drawing Sheets

(51) Int. Cl.
| | |
|---|---|
| *A61B 5/00* | (2006.01) |
| *A61B 5/01* | (2006.01) |
| *A61B 5/021* | (2006.01) |
| *A61B 5/145* | (2006.01) |
| *A61B 5/1455* | (2006.01) |
| *A61M 5/31* | (2006.01) |
| *G16H 30/40* | (2018.01) |
| *G06V 20/00* | (2022.01) |
| *G06V 20/64* | (2022.01) |
| *G16H 20/17* | (2018.01) |

(52) U.S. Cl.
CPC ...... *A61B 5/14532* (2013.01); *A61B 5/14551* (2013.01); *A61B 5/6898* (2013.01); *A61B 5/7282* (2013.01); *A61B 5/746* (2013.01); *A61M 5/3129* (2013.01); *G06V 20/00* (2022.01); *G06V 20/64* (2022.01); *G08B 21/0461* (2013.01); *G16H 30/40* (2018.01); *G16H 40/20* (2018.01); *A61B 2576/00* (2013.01); *A61M 2205/18* (2013.01); *A61M 2205/52* (2013.01); *A61M 2205/581* (2013.01); *A61M 2205/583* (2013.01); *G06V 2201/03* (2022.01); *G08B 21/0476* (2013.01)

(56) References Cited

U.S. PATENT DOCUMENTS

| | | | | |
|---|---|---|---|---|
| 2004/0103043 | A1* | 5/2004 | Reade | G06Q 30/0623 705/23 |
| 2009/0043253 | A1 | 2/2009 | Podaima | |
| 2009/0198733 | A1* | 8/2009 | Gounares | G16H 15/00 |
| 2010/0283601 | A1* | 11/2010 | Tai | A61J 7/0409 340/539.12 |
| 2010/0286609 | A1* | 11/2010 | Mahurkar | A61M 5/502 604/110 |
| 2011/0082711 | A1* | 4/2011 | Poeze | G06Q 10/109 600/300 |
| 2012/0241525 | A1* | 9/2012 | Borges | G06K 19/06112 235/494 |
| 2013/0110537 | A1 | 5/2013 | Smith | |
| 2013/0153662 | A1* | 6/2013 | Narasa Prakash | G06K 7/1486 235/462.07 |
| 2013/0345641 | A1 | 12/2013 | Cerman et al. | |
| 2014/0330579 | A1* | 11/2014 | Cashman | G06Q 10/1095 705/2 |
| 2015/0019234 | A1* | 1/2015 | Cooper | G16H 10/60 705/2 |
| 2015/0126963 | A1* | 5/2015 | Despa | G16H 10/60 604/154 |
| 2016/0012205 | A1* | 1/2016 | Saint | A61M 5/31528 604/189 |
| 2016/0092652 | A1* | 3/2016 | Stewart | G06F 16/24573 705/3 |
| 2016/0259913 | A1 | 9/2016 | Yu et al. | |
| 2016/0324727 | A1 | 11/2016 | Waugh et al. | |
| 2016/0338590 | A1* | 11/2016 | Sagalovich | A61B 1/07 |
| 2016/0379504 | A1* | 12/2016 | Bailey | G06V 40/20 434/219 |
| 2017/0056603 | A1* | 3/2017 | Cowan | A61M 5/007 |
| 2017/0286638 | A1 | 10/2017 | Searle et al. | |
| 2018/0247711 | A1* | 8/2018 | Terry | A61B 50/18 |
| 2018/0261322 | A1* | 9/2018 | Cheng | A61B 5/742 |
| 2018/0344941 | A1* | 12/2018 | Cowe | A61M 5/31595 |
| 2019/0117888 | A1* | 4/2019 | Burkholz | A61B 10/02 |
| 2019/0175104 | A1* | 6/2019 | Malik | A61B 10/0051 |
| 2019/0224406 | A1 | 7/2019 | Cowan et al. | |
| 2019/0341136 | A1* | 11/2019 | Hopper | H04W 4/023 |
| 2020/0297909 | A1* | 9/2020 | Suljevic | A61M 1/281 |
| 2021/0035670 | A1* | 2/2021 | Abrahamsson | G16H 40/20 |
| 2021/0110897 | A1* | 4/2021 | Ginsburg | G16H 10/60 |
| 2022/0027629 | A1* | 1/2022 | Case | G02B 27/0172 |

* cited by examiner

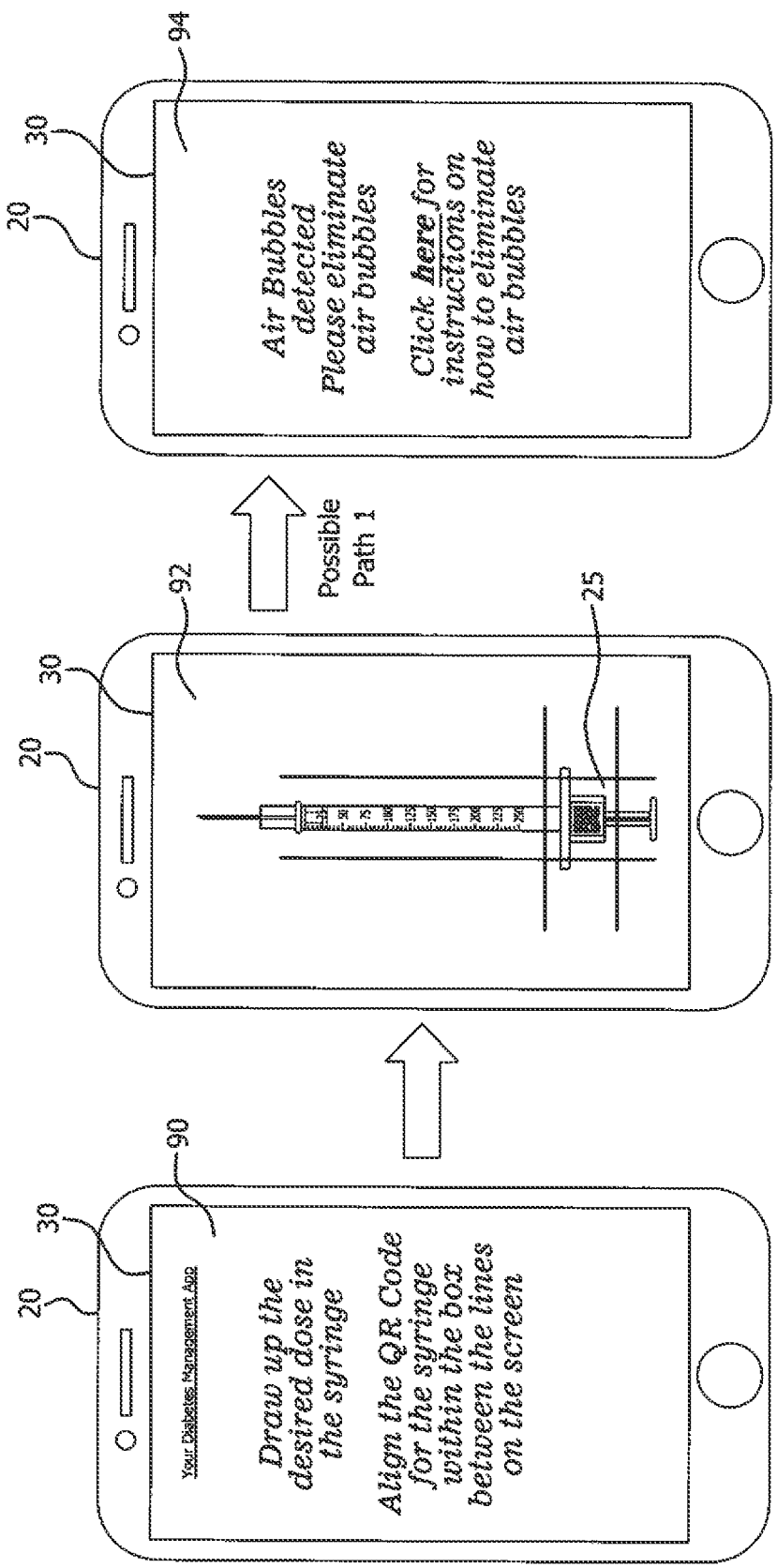

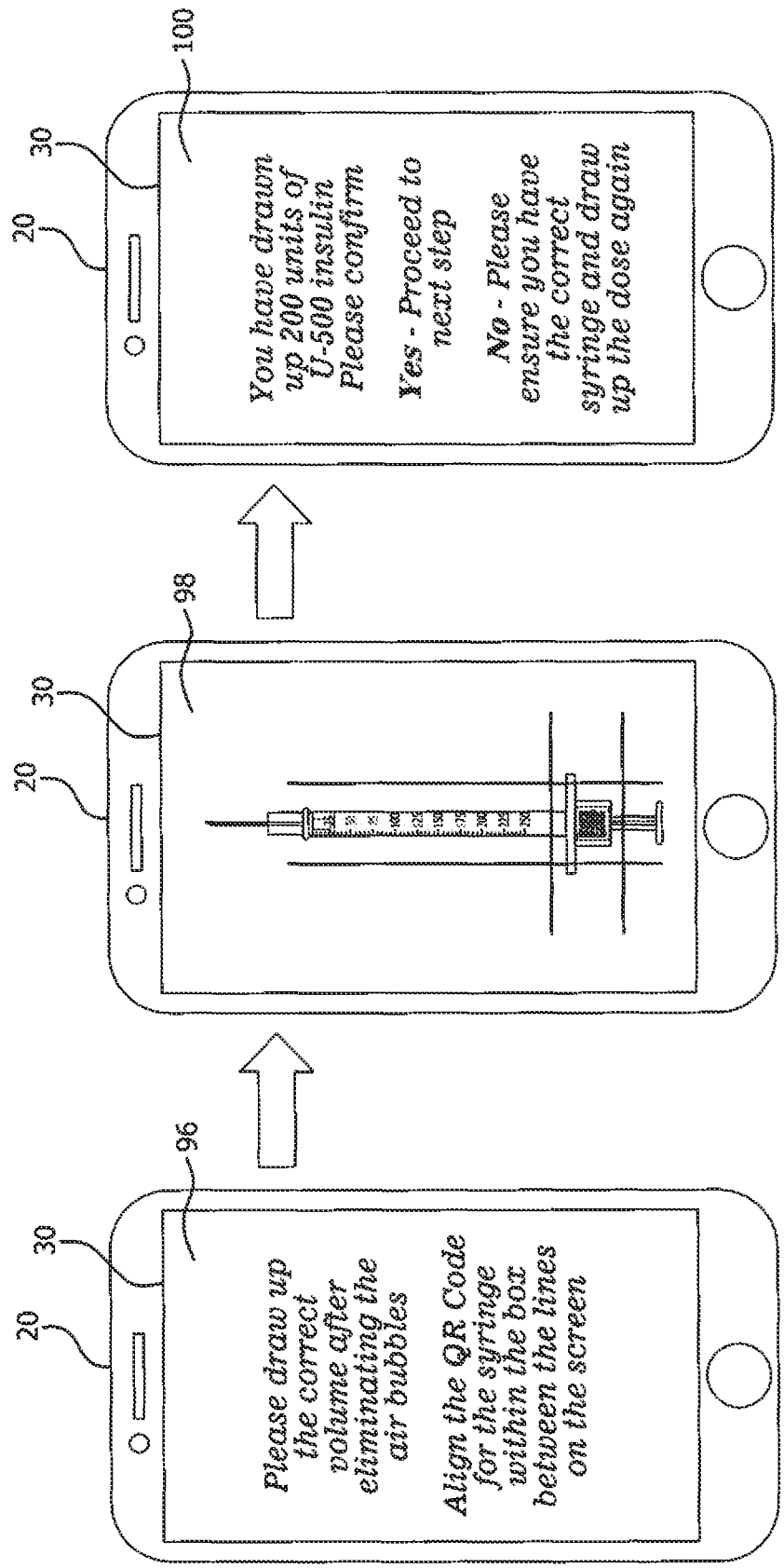

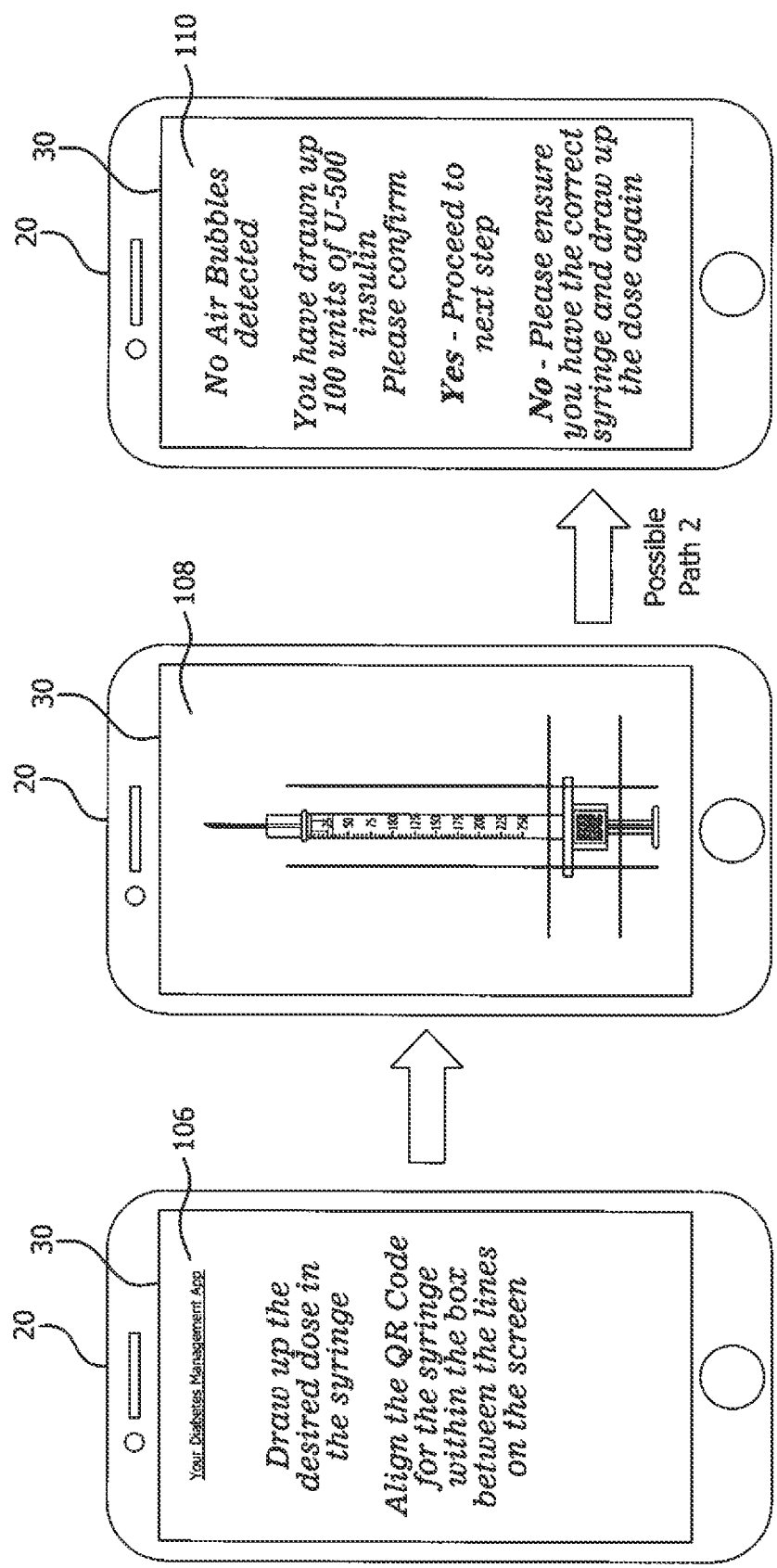

SYSTEMS, APPARATUSES AND METHODS FOR CAPTURING IMAGES OF MEDICAL CONDITION MANAGEMENT EVENTS AND RELATED EQUIPMENT WITH SMARTPHONE AND RELATED APP THAT PROCESSES IMAGES TO REDUCE MEDICAL ERRORS

BACKGROUND

Field

Illustrative embodiments relate generally to using a portable, handheld device such as a smartphone to capture images of medical condition management events involving medical equipment, and related smartphone app that processes the images and interacts with user(s). Illustrative embodiments relate generally to a medical event image capture app that processes images of medical condition management events to reduce medical errors that can be caused by using incompatible injection device and drug, drawing incorrect drug amount into syringe or injection pen prior to delivery, using contaminated or incorrect drug or damaged or incorrect injection supplies, etc.

Description of Related Art

Medication non-adherence is an issue of global importance, particularly with regard to diabetes care. Fifty percent (50%) of all patients do not take their medication as prescribed. Non-adherence directly contributes to hundreds of thousands of deaths and billions of dollars in avoidable medical and related costs.

There are smartphone apps that use a picture of a prescription label to help a patient reorder when their supply of prescribed medication is low. However, these apps do not directly identify the medication or the dose prior to the patient taking the medication, and are not useful for syringes or pen injectors.

There are smartphone apps that assist users with recording medical events such as injections. There are smart injection devices that can assist users with automatically logging dialed amounts for delivery and/or delivered amounts of medication.

Nonetheless, there remains a continuing need for methods and devices to assist users (e.g., patients, their caregivers, their healthcare providers and other medical condition management stakeholders such as payers/insurance companies, pharmacies, and medical products suppliers and distributors) in the acquisition and use of information related to medical condition management events to prevent medical errors such as medication delivery errors, as well as to improve related processes such as replenishment of medical supplies, tracking compliance with medical condition management protocol or regimen, and information sharing among medical condition management stakeholders for optimal patient treatment plan of care, billing and insurance coverage purposes.

SUMMARY

The above and other problems are overcome, and additional advantages are realized, by illustrative embodiments.

In accordance with aspects of illustrative embodiments, a portable device for capturing images of medical events to reduce medical errors comprises: an imaging device for imaging at least one medical product in use during a medical event; a memory to store images captured by the imaging device and program instructions for processing captured images; a user interface configured to generate an output to a user, and a processor. The processor is adapted to execute the program instructions to analyze a captured image associated with the medical event to detect a characteristic of the medical product selected from the group consisting of an indicia on the medical product, and a designated attribute of the medical product, and to analyze the detected characteristic to determine when a medical error occurs. The medical error corresponds to when the medical product is incompatible with the medical event, mishandled by the user, or malfunctioning. The processor is configured to generate an output to the user via the user interface comprising an alert related to the medical error.

It is an aspect of illustrative embodiments to provide a portable device wherein at least one captured image in its memory corresponds to a medical event involving at least two medical products used together, and its processor is configured to analyze the at least one captured image to detect indicia on each of the at least two medical products, analyze the indicia on each of the at least two medical products using previously stored medical product data that locally or remotely accessible by the processor, the previously stored medical product data comprising indicia for respective ones of a plurality of different medical products and, for each medical product among the plurality of different medical products, the corresponding indicia of one or more other medical products indicated as compatible with that medical product, and generate an output to the user when the processor determines that the at least two medical products are incompatible according to the previously stored medical product data.

It is an aspect of illustrative embodiments to provide a portable device, wherein the medical device is a medication delivery device having indicia, and the processor is configured to analyze a captured image of the medication delivery device and detect the indicia, and analyze the or other captured image of the medication delivery device medication and detect an amount of medication indicated for delivery by the medication delivery device. Further, using previously stored medical product data that locally or remotely accessible by the processor, the previously stored medical product data comprising a plurality of different medication delivery devices and their respective indicia and, for each medication delivery device among the plurality of different medication delivery devices, specifications for designated amounts of medication that can be delivered via that medication delivery device, the processor determines the designated amount of medication corresponding to the medication delivery device associated with the indicia detected from the captured image, and generates an alert via the user interface when the detected amount of medication indicated for delivery is determined to be different from the designated amount of medication.

For example, the detected amount of medication indicated for delivery corresponds to a marking in the captured image that is associated with at least one of a dose input on an injection pen, or a level indicator on a syringe barrel that is adjacent to fluid level in the syringe. As a further example, the processor uses an algorithm chosen from a two-dimensional image processing algorithm and a three-dimensional image processing algorithm to analyze the or other captured image and detect the amount of medication indicated for delivery by the medication delivery device.

It is an aspect of illustrative embodiments to provide a portable device, wherein the medical device is a medication delivery device having indicia, and the processor is configured to analyze a captured image of the medication delivery device and detect the indicia. Further, using previously stored medical product data that is at least one of locally and remotely accessible by the processor, the previously stored medical product data comprising a plurality of different medication delivery devices and their respective indicia and, for each medication delivery device among the plurality of different medication delivery devices, specifications for designated amounts of medication that can be delivered via that medication delivery device, the processor determines the designated amount of medication corresponding to the medication delivery device associated with the indicia detected from the captured image, and generates an alert via the user interface when a prescribed amount of medication indicated for delivery is determined to be different from the designated amount of medication.

The processor is further configured, for example, to analyze the or other captured image of the medication delivery device medication and detect an amount of medication indicated for delivery by the medication delivery device, the detected amount of medication indicated for delivery corresponding to a marking in the captured image that is associated with at least one of a dose input on an injection pen and a level indicator on a syringe barrel that is adjacent to fluid level in the syringe, and generate an alert via the user interface when the prescribed amount of medication indicated for delivery is determined to be different from the detected amount of medication indicated for delivery.

It is an aspect of illustrative embodiments to provide a portable device, wherein the medical device is a medication delivery device, and the processor is configured to analyze the captured image of the medication delivery device, detect an amount of medication indicated for delivery by the medication delivery device, and store the detected amount of medication indicated for delivery in the memory device. The detected amount of medication indicated for delivery corresponds, for example, to a marking in the captured image that is associated with at least one of a dose input on an injection pen and a level indicator on a syringe barrel that is adjacent to fluid level in the syringe.

It is an aspect of illustrative embodiments to provide a portable device, wherein the program instructions comprise at least one of a two-dimensional image processing algorithm and a three-dimensional image processing algorithm used by the processor to analyze the captured image.

It is an aspect of illustrative embodiments to provide a portable device, wherein the processor is configured to analyze at least one captured image to detect a characteristic of the medical product comprising at least one designated attribute of the medical product selected from the group consisting of selected color of medical product, selected dimension of medical product, selected form factor of medical product, presence of safety mechanism on medical product, absence of safety mechanism on medical product as compared with stored image of medical product having safety mechanism, and analyze the detected characteristic to determine whether a medical error has occurred using previously stored medical product data that is at least one of locally and remotely accessible by the processor, the previously stored medical product data comprising designated specifications for image characteristics of the medical product corresponding to the at least one designated attribute.

For example, the medical product is a liquid medication drawn into a syringe, and the at least one designated attribute of the liquid medication is selected from the group consisting of opaqueness of the liquid medication, presence of bubbles in the liquid medication, presence of particulates in the liquid medication. As a further example, the previously stored medical product data comprises designated specifications for image characteristics of the at least one designated attribute of the liquid medication.

It is an aspect of illustrative embodiments to provide a portable device that is at least one of a mobile phone and a computing device with wireless communications interface, and the memory is configured to store at least one of an integrated disease management (IDM) app, the IDM app comprising an IDM personal app operated by a user who is a patient and/or an IDM professional app operated by a healthcare professional. The processor is further adapted to execute instructions in accordance with the IDM app to operate the portable device in a cloud configuration with a remote IDM system whereby the IDM app transfers data to and receives data from the IDM system during an app session.

It is an aspect of illustrative embodiments to provide a portable device that operates in accordance with the IDM personal app to transfer to and store informatics from the captured images at the IDM system, the informatics selected from the group consisting of dose amount determined from at least one of the captured images, medical event date and/or time stamps determined from at least one of the captured images, and/or medical products identified from at least one of the captured images.

It is an aspect of illustrative embodiments to provide a portable device that operates in accordance with the IDM professional app to determine patient information from the informatics stored in the IDM system, the patient information comprising at least one of compliance data for a prescribed regimen based on the informatics related to dose amount and medical event date and/or times, medical product prescription renewal data based on the informatics related to the medical products identified from the captured images and medical event date and/or times corresponding to use of these medical products, and/or billing data corresponding to medical products identified from the captured images and medical event date and/or times corresponding to use of these medical products.

It is an aspect of illustrative embodiments to provide a portable device that can be connected wirelessly to at least one other medical condition management device and obtain medical event information therefrom. The processor is further adapted to execute instructions in accordance with the IDM app to transfer the medical event information to the IDM system.

It is an aspect of illustrative embodiments to provide a portable device, wherein the cloud configuration comprises a private cloud and a public cloud, and the portable device operates in accordance with the IDM app to determine whether at least one of the informatics and other data related to the user that is stored in the memory is proprietary data or non-proprietary data and to selectively transfer the proprietary data via the private cloud and the non-proprietary data via the public cloud.

It is an aspect of illustrative embodiments to provide a portable device for capturing images of medical events that comprises: an imaging device for imaging at least one medical product in use during a medical event; a memory to store images captured by the imaging device and program instructions for processing captured images; a user interface configured to generate an output to a user, and a processor adapted to execute the program instructions to analyze a captured image associated with the medical event to detect a characteristic of the medical product selected from the group consisting of an indicia on the medical product, and a designated attribute of the medical product, store data related to the detected characteristic in the memory, and generate an output to the user via the user interface using the data related to the detected characteristic.

It is an aspect of illustrative embodiments to provide a portable device that is a monitor for a selected medical condition, and the detected characteristic is a monitored parameter detected by the monitor and indicated via a user interface associated with the monitor.

It is an aspect of illustrative embodiments to provide a portable device with a processing that is further adapted to execute the program instructions to log a date and/or time associated with the detected characteristic.

It is an aspect of illustrative embodiments, the monitor is selected from the group consisting of a pulse oximeter, thermometer, blood pressure monitor, and blood glucose monitor.

Additional and/or other aspects and advantages of illustrative embodiments will be set forth in the description that follows, or will be apparent from the description, or may be learned by practice of the illustrative embodiments. The illustrative embodiments may comprise apparatuses and methods for operating same having one or more of the above aspects, and/or one or more of the features and combinations thereof. The illustrative embodiments may comprise one or more of the features and/or combinations of the above aspects as recited, for example, in the attached claims.

BRIEF DESCRIPTION OF THE DRAWINGS

The above and/or other aspects and advantages of the illustrative embodiments will be more readily appreciated from the following detailed description, taken in conjunction with the accompanying drawings, of which:

FIGS. 7A, 7B, 7C, 7D, 7E, 7F, 7G and 7H and FIGS. 8A, 8B, 8C, 8D and 8E and FIGS. 9A, 9B and 9C illustrate example GUI screens generated by the device with a medical event image capture app of FIG. 1 in accordance with an illustrative embodiment.

Throughout the drawing figures, like reference numbers will be understood to refer to like elements, features and structures.

DETAILED DESCRIPTION OF ILLUSTRATIVE EMBODIMENTS

Figure 1:
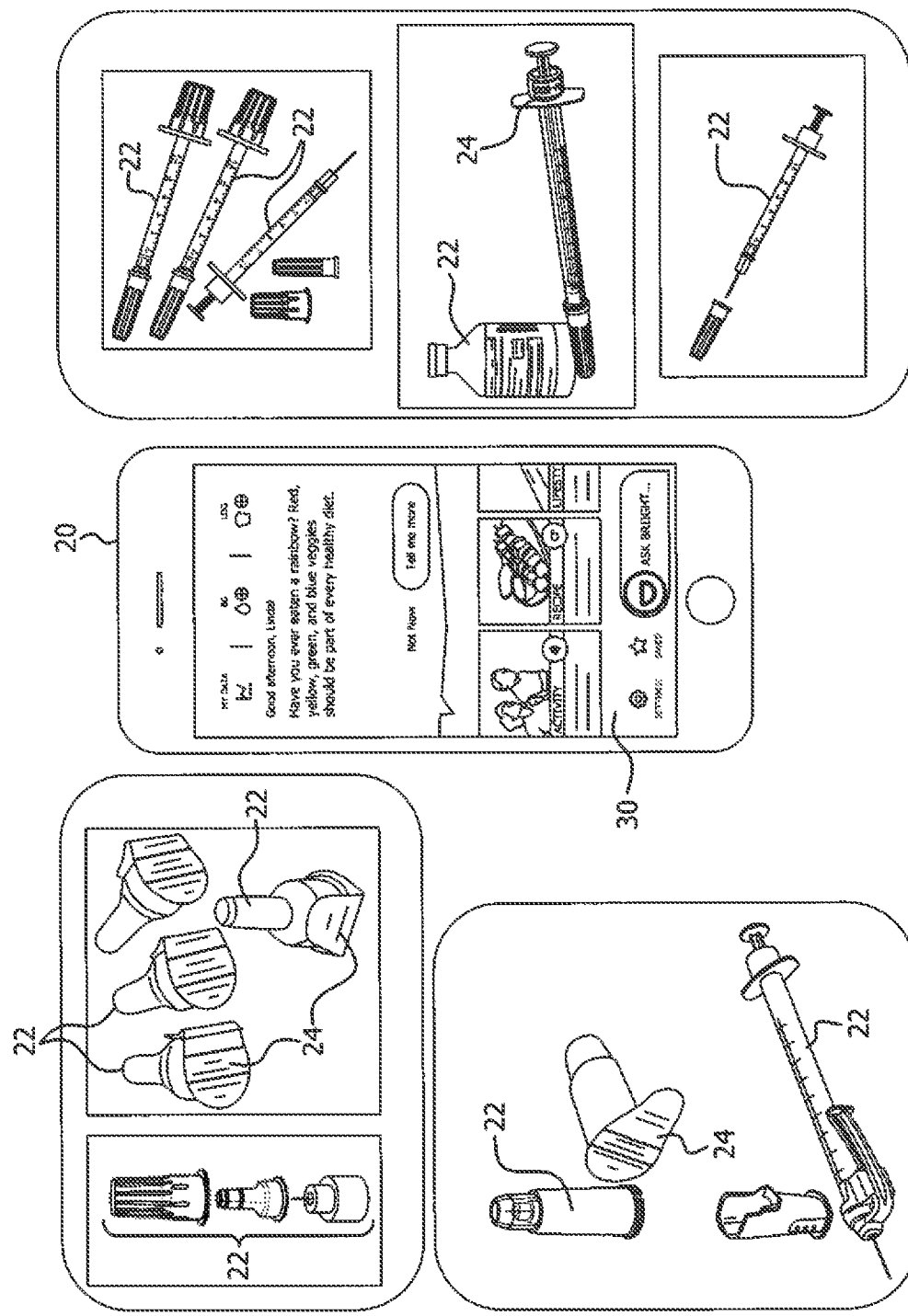
FIG. 1 depicts a device with a medical event image capture app and different types of example medication delivery products in accordance with an illustrative embodiment.

Reference will now be made in detail to illustrative embodiments, which are illustrated in the accompanying drawings. The embodiments described herein exemplify, but do not limit, the illustrative embodiments by referring to the drawings.

Figure 2:
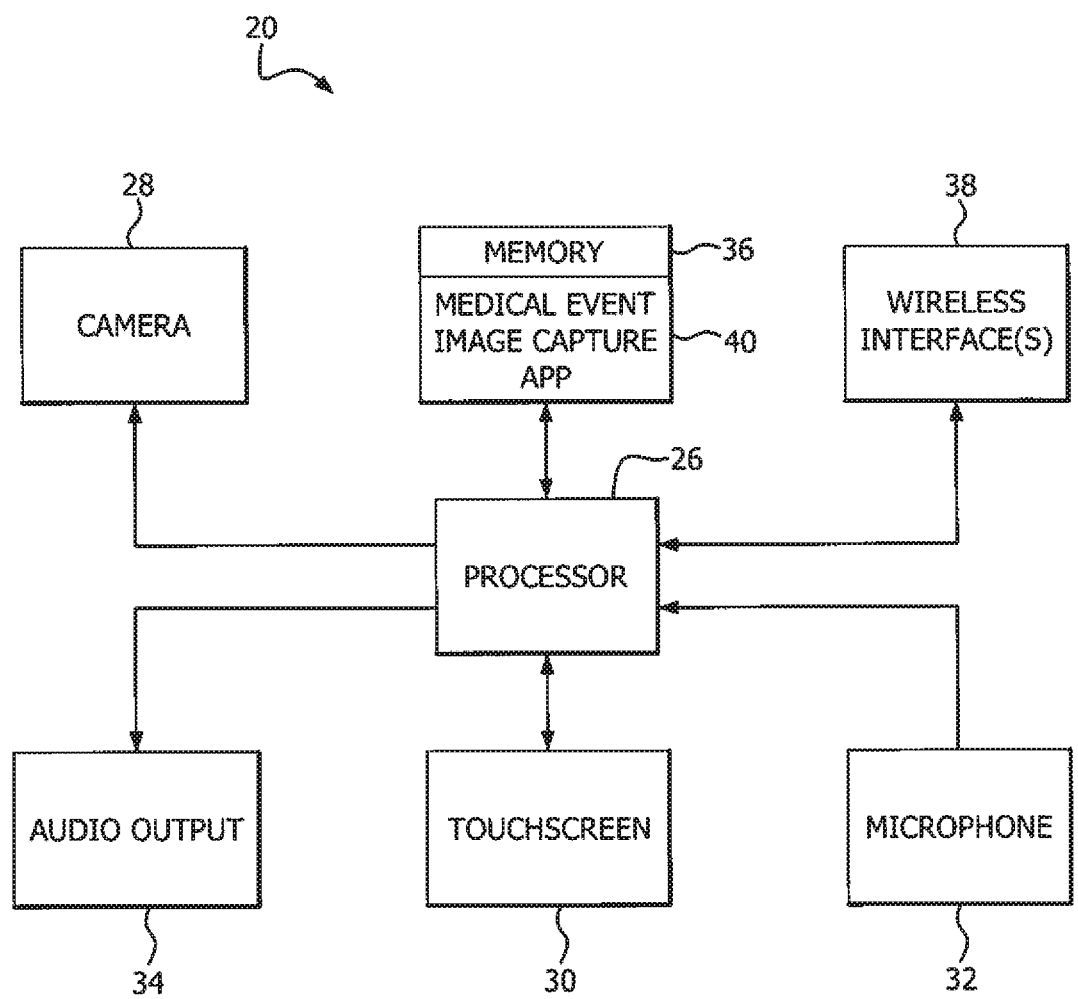
FIG. 2 is a block diagram of the device with a medical event image capture app of FIG. 1 in accordance with an illustrative embodiment.

With reference to FIGS. 1 and 2 and in accordance with illustrative embodiments, a medical condition management event image capture app 40 is described herein that can be a standalone app on a smartphone 20 or other portable device with camera (e.g., an iPad), or can be provided as an enhancement to a digital health (DH) app for a smartphone or other smart, connected device. The medical event image capture app 40 uses an image of indicia 24 on medical products 22, or an image of the medical product 22 (e.g., a camera image of a product 22 with indicia 24 as indicated at 25 in FIG. 7B), to automate access to and/or recording of additional informatics to assist with medical condition management. The additional informatics from the captured medical product images are used by different functions of the app 40 to reduce medical errors (e.g., injections of the wrong amount of medication due to medical product misuse or defect).

FIG. 1 shows an example smartphone 20 with the medical event image capture app 40 and a plurality of example medical products 22 such as, but not limited to, injection pen needle assemblies and related injection pen products, syringe injection products, and syringe safety injection products (e.g., BD AutoShield Duo™ Pen Needle and BD SafetyGlide™ 6 mm insulin syringe, which are designed to help prevent inadvertent needlestick injury during injections, particularly in clinical settings), among others. The products 22 can be provided with different types of indicia 24 that are printed or inscribed directly thereon, or applied indirectly to products 22 using labels comprising the indicia, for example. The indicia 24 can be one or more of alphanumeric text, symbols, different colors, and optically recognized codes such as bar codes, Quick Response (QR) codes, and universal product (UPC) codes, among other types of indicia whose image can be captured via a camera and, in accordance with an aspect of the illustrative embodiments, processed for decoding into related information about the item to which the insignia is applied or related event involving use of the item.

Illustrative embodiments described herein are with reference to diabetes management and injection of insulin, for example. It is to be understood that the indicia, image capture and app processing of images to obtain medical condition management event informatics, and human machine interactions based on those informatics, in accordance with the illustrative embodiments can be used for reducing errors with respect to management or treatment of other medical conditions that require use of various devices and medical condition management procedures such as surgical instruments, blood collection and delivery products, delivery of other medications besides long-acting and short-acting insulins (e.g., drugs related to hormone therapies, GLP-1s, rheumatoid arthritis or Crohn's disease treatment, and other drugs that require dosing regimens and a certain level of control and monitoring), and so on. For example, the illustrative embodiments can be used to reduce medical errors associated with self-injection using other types of medications, correct use of surgical tools for a selected medical procedure, correct use of equipment for IV delivery of medical fluids to patients, and so on. Also, illustrative embodiments described herein are advantageous to a variety of different injection applications besides human patient injection events such as veterinary treatments that employ injection regimens.

Example embodiments are described herein with respect to diabetes management and related injection products and events. It is to be understood, however, that these example embodiments can be implemented with respect to other types of human and non-human animal medical conditions, medical events and related condition management products. Further, the medical events need not be related to drug administration (e.g., can instead be for surgical instrument preparation). Further, any drug administration application need not be limited to injections. For example, the app 40 can be used for informatics capture and management of an oral medication regimen and/or topical treatment regimen. With regard to diabetes management, diabetes care companies manufacture a very large number of insulin delivery or injection products that are integral to the diabetes therapy of diabetic patients worldwide. These injection products are utilized by patients who self-inject and caregivers of diabetic patients, and can include, but are not limited to, injection pens, pen needle assemblies, syringes, different sizes of needles, different types of insulin in different form factors (e.g., vials, pre-filled syringes, cartridges for injections pens). For example, a patient's injection regimen can require a selected type of syringe, needle and type of insulin such that using the wrong type of insulin or syringe can impact the accuracy of the intended dosage amount.

In accordance with illustrative embodiments, a device 20 with the medical event image capture app 40 (1) provides image capture of medical event device(s) and image processing to determine one or more of medical equipment correctness, accuracy of delivered amount, and medication status, and (2) generates alerts and user guidance via a graphical user interface on a device 20 to reduce medical errors. FIG. 2 is a block diagram depicting an example device 20. The device 20 is referred to as a smartphone, but it is understood that the device 20 can be a dedicated medical management device or other portable, handheld device (e.g., iPad) with an indicia image capture or reader device 28 such as a camera. The device 20 comprises a processor 26, and a memory 36 that can store a medical event image capture app 40 in accordance with an illustrative embodiment, along with other device data, images and apps. The device 20 can have one or more wireless communication interface(s) 38 such as a Bluetooth®-enabled wireless communications interface and a cellular communications interface, for example. The device 20 can also have different user interfaces such as one or more of a microphone 32, touchscreen 30 or other display device that generates graphical user interface (GUI) screens such as those of the medical event image capture app 40, optional keypad or other user input device (not shown), and an audio signal output device (e.g., speaker or buzzer) 34.

The medical event image capture app 40 is program code that provides indicia and/or injection product image capture operations, and captured image processing operations. The captured image processing operations can (1) decode or otherwise discern artifacts and related informatics from indicia and other image elements in the captured image, and (2) perform human machine interaction (HMI) operations or other logical operations that alert a user regarding a selected informatic and request input or otherwise educate the user about a related medical event. For example, the image capture operation captures images from the device camera 28. The captured image processing operations can implement a two-dimensional (2D) image and/or or three-dimensional (3D) image processing algorithm to detect selected artifacts from the captured image(s). The captured image processing operations can optionally include a recognition operation such as a QR code reader, bar code or UPC code reader, or optical character recognition (OCR) operation within the app 40. The HMI or other operations of the medical event image capture app 40 determine how the detected artifacts impact a medical condition management event and generate GUI screens or other HMI outputs (e.g., audible inquiry or message output to the user by the speaker 34) to educate the user or request user input.

In accordance with illustrative embodiments, at least three applications for the medical event image capture app 40 are described with reference to FIGS. 3A to 3E, FIGS. 4A and 4B, and FIG. 5, respectively, that is, (1) confirmation of correct injection device, (2) dose confirmation, and (3) detection of defective drug, device or improper use. The app 40 can provide only one of these applications, a subset of any two of these applications, or all of these applications.

With regard to the first application (i.e., confirmation of correct injection device 22) of the medical event image capture app 40, and with reference to FIGS. 3A through 3E, a smartphone 20 having the medical event image capture app 40 is depicted with one or more devices 22 (e.g., a vial of insulin and a syringe) having indicia 24 in an image range 42 of the smartphone camera 28. The app 40 can recognize correct injection device by virtue of image recognition, QR code or other machine-readable code, color of the markings on the syringe or vial, or other distinguishing features. Particularly in the case of syringes, there can be a variety of needle sizes, barrel capacities and scale markings that are unique to a certain type of drug. Examples illustrated with insulin syringes are shown below, but are representative of most treatments using different types of medications. Some injection products, such as those commercially available from Becton, Dickinson and Company or "BD," already have unique markings that indicate that they should be used with certain types of drugs. These unique markings or indicia (e.g., a QR code) can be made readable by the app 40 via the app's image processing algorithm to ensure that the patient or caregiver is using the correct kind of syringe for the correct insulin and thereby reduce medication errors.

For example, the app 40 can be programmed to consult locally stored or remotely accessed information comprising tables or other data memory structures for these unique markings 24 related to particular injection products 22 for comparison or other analysis to identify the item 22 in the captured image. Alternatively, these unique markings or indicia 24 can be detected via the app 40 to automatically navigate to user to online education materials (e.g., videos) on injections or other medical condition management skills. For example, if the indicia 24 is a QR code, the app 40 can have a QR code scanner that converts the indicia 24 to some useful form (such as a standard URL for a website). The form can be a symbol or character that classifies the device (e.g., as belonging to a class of related products as described below), or the decoded QR code can direct the smartphone 20 to the URL of a web-based table via the smartphone's browser to do look-up operations regarding related products. Thus, the camera 28 in a smartphone 20 equipped with the app 40 having an integrated indicia reader can scan the image of the QR code or other indicia 24 on an item 22 to display text (e.g., contact information or instructions via a GUI screen 30), or connect to a wireless network (e.g., to a HCP repository), or open a web page in the smartphone's browser. The app 40 can also generate GUI screens or other alerts when medical devices or products 22 appear to be mismatched as illustrated in FIG. 7F.

Figure 3A:
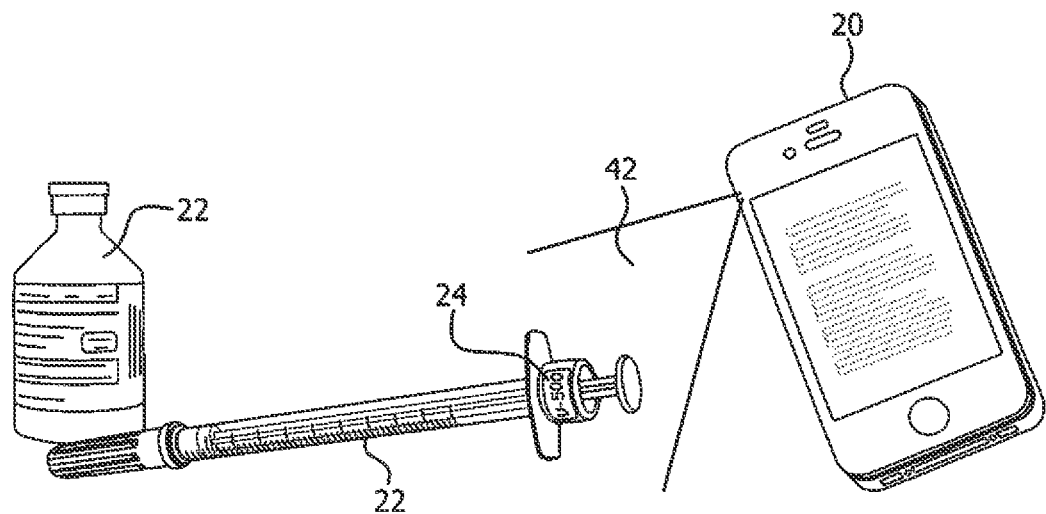
FIGS. 3A, 3B, 3C, 3D, 3E, 4A, 4B and 5 each depict the device with a medical event image capture app of FIG. 1 capturing an image of an example medication delivery product in accordance with an illustrative embodiment.

In the example depicted in FIG. 3A, the medical event image capture app 40 can be programmed to detect an alphanumeric indicia 24 (e.g., "U-500") in the captured image of an insulin vial and syringe held in front of the camera 28. The app 40 can be programmed to then consult locally stored or remotely accessed information comprising codes or indicia that correspond to respective families of medical products that are compatible when used together for injection of accurate doses (e.g., different sizes of syringes and corresponding types of insulin) such that the app 40 can confirm whether or not the user is using compatible devices from the same family medical devices for effective or accurate dosing.

Figure 3B:
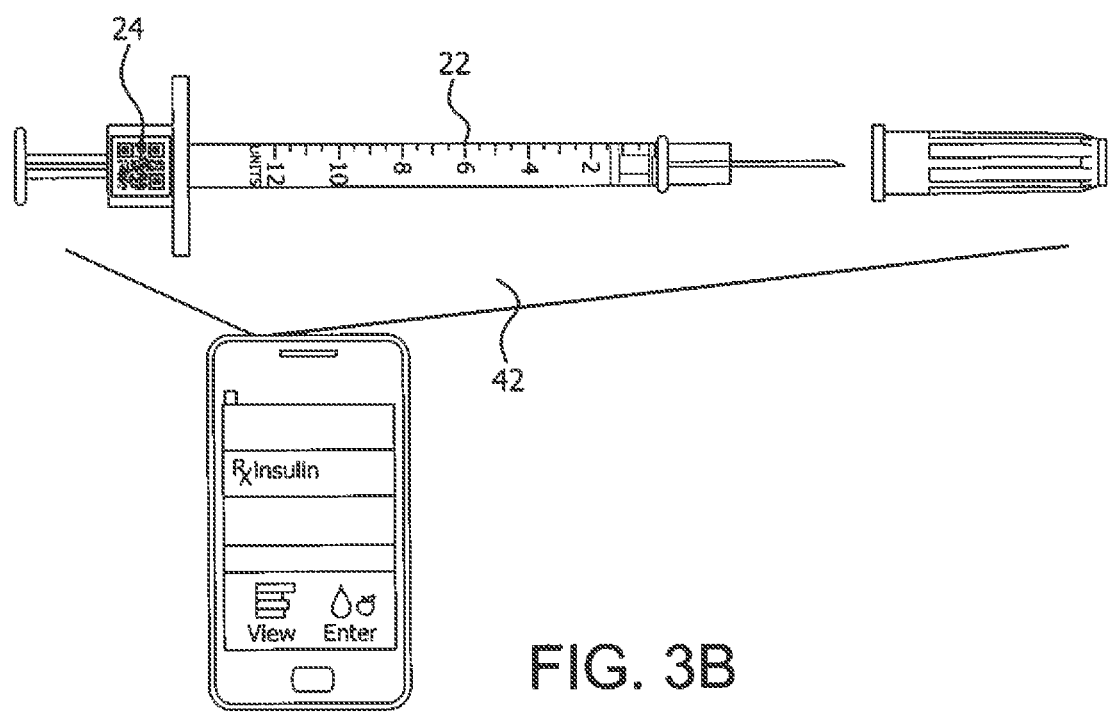

With continued reference to FIG. 3A, a diabetes care insulin and/or injection supplies manufacturer generally provides indicia (e.g., Stock Keeping Unit (SKU) numbers or other product identifying indicia) on their respective products (e.g., syringes, insulin pens, needle assemblies, insulin vials and cartridges, injection safety products, and the like). In accordance with an aspect of illustrative embodiments, manufacturers and other injection supplies companies can generate a table of compatible injection products wherein product codes of selected products are linked to a product family that is useful to deliver an injection, and the product family is given a selected code (e.g., alphanumeric nomenclature or other indicia that is machine-readable such as a QR code 24 as shown in FIG. 3B). When the user operates a smartphone 20 with the medical event image capture app 40 to capture an image of the items 22 the user is employing to deliver a self-injection, or injection to a patient, the items 22 in the view range 42 of the smartphone's camera 28 are captured in an image and the processor 26 processes the image in accordance with the app 40.

The captured image can include image pixels representing items 22 in FIG. 3A, that is, a vial and a syringe, for example. It is to be understood the images of respective items 22 in FIG. 3A being used for an injection can be captured separately, although this is less convenient to the user, and/or can be processed separately via the medical event image capture app 40 to identify indicia 24 or other event information such as dose capture or presence of bubbles as described below. The processor 26 can be controlled by the app 40 to process the image pixels representing the captured image items 22 using a 2D and/or 3D image analysis algorithm that is configured to identify one or more indicia 24 on the items 22 such as a product code and/or a product family code per item 22. Once the indicia 24 are parsed from the image pixel data, the indicia 24 are decoded or otherwise identified.

For example, with reference to FIG. 3B, a U40 syringe 22 is shown with an example of a QR code 24 that could be put on as a part of the manufacturing process. The QR code reads: 0.3 ml×12.7 mm U40. When the user scans the code prior to injection, the app 40 recognizes the device 22 and confirms that a correct device 22 is being used, or warns the user if that is not the case. For instance, using a U40 syringe with a U100 or U500 insulin would result in incorrect dosage of insulin delivered.

The indicia 24 can be a particular color on a label, or an alphanumeric product name (e.g., U-500), a product code (e.g., the QR code 24 on the syringe 22 in FIG. 3B), or a product family (i.e., with or without a product code) that is identified in a QR code or other machine-readable code, or a combination of indicia. The product family code can be, for example, a single character or multiple characters, and the characters can be alphanumeric characters or symbols or other indicia. In an example, a table of compatible injection products can comprise product families "A, . . . , N" and can be locally or remotely stored with respect to the device 20. If all of the captured image items 22 has the same product family code "A", then the processor 26 determines that the items 22 are compatible and optimized to give an accurate dose. On the other hand, if processor 26 identifies two or more different product family codes (e.g., a QR code on a vial indicating a product family "A" and a QR code on a syringe indicating a product family "B"), in the image(s) of the captured items 22, then the processor 26 can be operated via the medical event image capture app 40 to generate an alert to the user. For example, the processor 26 can generate a GUI screen displayed on the touchscreen 30 that advises the user of the detected item's 22 incompatibility and optionally recommends a different size syringe from product family "A," in lieu of the image captured family "B" syringe, for use with the detected vial from family "A".

Figure 3C:
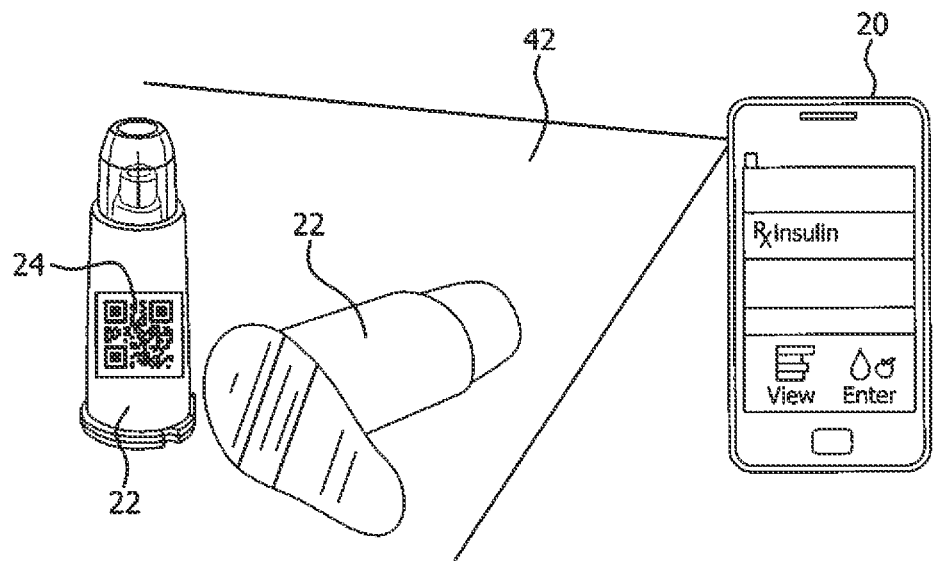

With reference to FIG. 3C, a BD AutoShield Pen Needle 22 is depicted with an example of a QR code 24 that could be used to help drive better usage methodology. In this case, the QR code 24 reads "Best Injection Practices" and triggers a feature within the medical event image capture app 40 to playback local content, or takes the user to a website via the smartphone 20 browser, that demonstrates good injection practice. Similar QR codes can also be used to enable patient education on other medical condition management topics.

Example product families in locally or remotely stored tables or other data memory structures accessed via the app 40 can also be defined depending on healthcare setting, that is, a clinical setting wherein a healthcare provider (HCP) delivers an injection to a patient, or a home health setting wherein a patient self-injects or has a home health caretaker or family member deliver the injection to the patient. With further reference to FIG. 3C, the medical event image capture app 40 can optionally be configured to generate an alert to a HCP when the captured image of an injection product lacks a selected product family code 24 designated for injection safety products. The alert can be a reminder to a HCP to use an injection safety product (e.g., BD AutoShield Pen Needle or a BD SafetyGlide 6 mm insulin syringe) that are designed to help prevent inadvertent needlestick injury during injections that can occur in clinical settings.

Figure 3D:
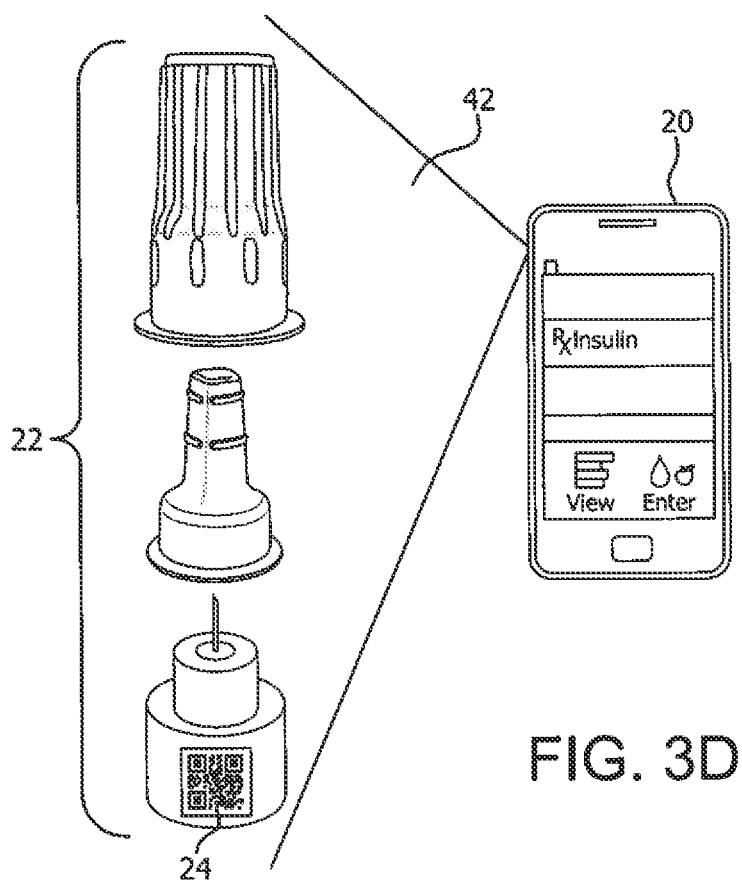
Figure 3E:
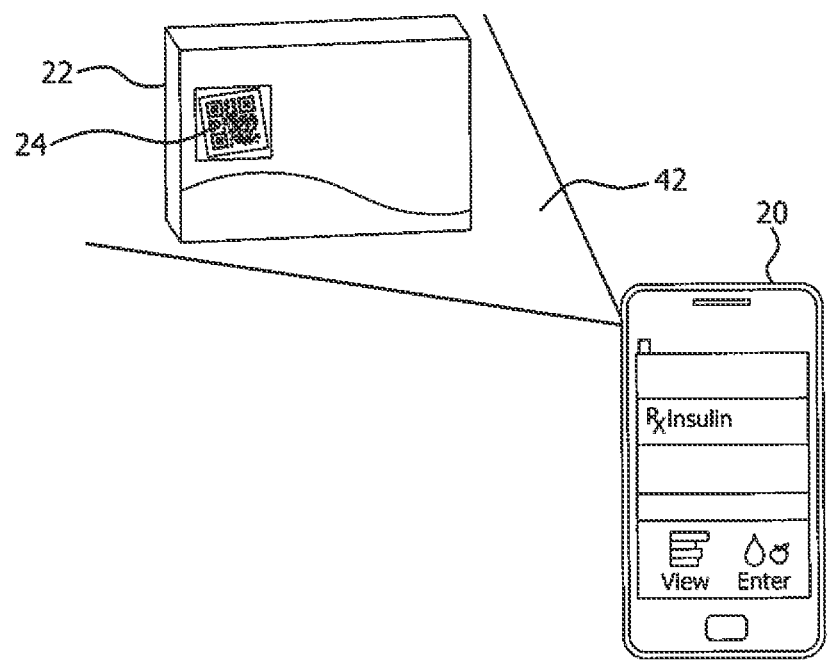

In accordance with an aspect of the illustrated embodiments, the image captured items 22 can be insulin pen injection supplies, versus syringe injection supplies, such as a pen needle 22 with indicia 24 as depicted in FIG. 3D, or a package 22 of pen needles of a selected size and indicia 24 on the package 22 as depicted in FIG. 3E. For example, QR codes 24 on pen injectors 22 can also be leveraged to look at the treatment as a composite of injector and pen needles instead of in isolation of each other. The processor 26 can be programmed in accordance with the medical event image capture app 40 to capture an image of the item 22 and process the image to determine the type of product based on the code 24 and/or color and alphanumeric information on the product label, or based on other physical characteristics of the image captured item 22. The processor 26 can perform a look up operation in a local or remote table of compatible injection products and alert the user (e.g., via a GUI screen on the touchscreen 30) when the product and/or product family code 24 is not compatible with the type of injection pen or its insulin, which can be identified in a settings profile in the app 40. In addition, the processor 26 can control the smartphone 20 to navigate to a particular URL identified with respect to the item code 24 (e.g., encoded in the QR code 24) to show a video or website of information to better educate the user about optimal injection technique or product 22 usage.

Figure 4A:
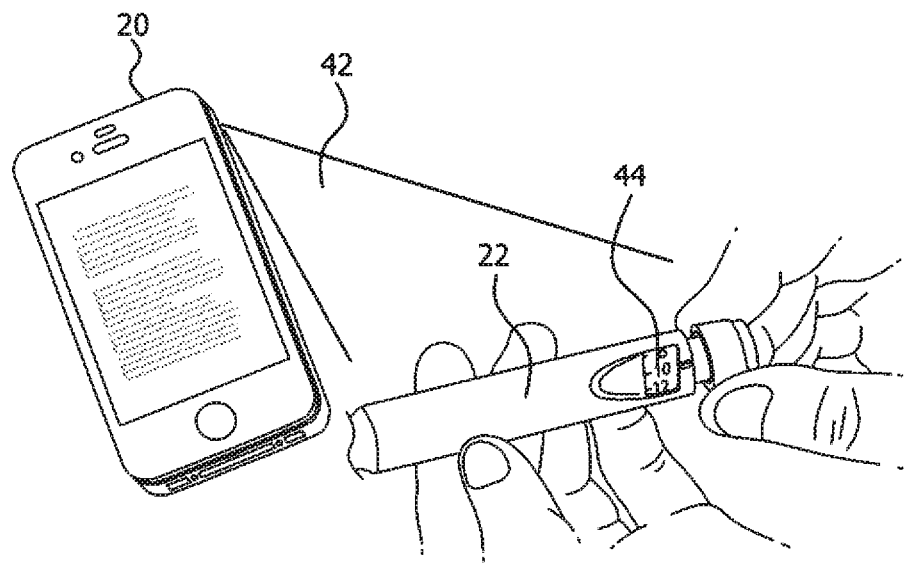
Figure 4B:
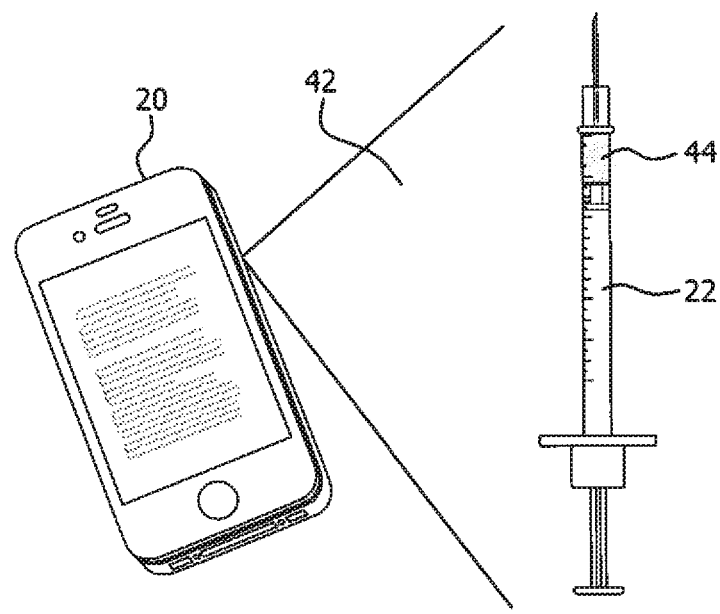

With regard to a second application (i.e., dose confirmation) of the medical event image capture app 40 and FIGS. 4A and 4B, in accordance with illustrative embodiments, the medical event image capture app 40 is configured to process captured images to determine amount of medication to be delivered. For people administering injections to oneself or to others, dose measurement, dose confirmation and tracking can be a challenge that can be alleviated by functions of the medical event image capture app 40. For example, the app 40 can also be used to ensure that the patient is drawing up the correct dose, particularly in the case of the syringe but also in the case of injection pens. In addition to dose confirmation, the combination of app 40 functions that determine correct device and correct dosage is expected to drive improved compliance to therapy, reduced likelihood of medication errors, and better outcomes for the patient.

With reference to FIGS. 4A and 4B, the item 22 being used for an injection can be placed within the view range 42 of the camera 28. An image is captured that comprises pixels that represent an injection level or delivered amount indicia. The medical event image capture app 40 can be provided with a 2D and/or 3D image processing algorithm configured to discern, for example, a syringe plunger location 44 (FIG. 4B) that corresponds to a drawn amount (i.e., amount to be injected via the syringe 22), or an injection pen dial indicia 44 (FIG. 4A) that corresponds to a dialed amount of medication to be delivered via the injection pen.

Apps exist that allow a smartphone to wirelessly communicate with wireless-enabled injection pens to receive dialed and/or delivered dose information wirelessly. These injection pens therefore are subject to additional complexity and therefore extra cost because they require a wireless communication interface to make the injection pen into a wireless-enabled device. By contrast, the medical event image capture app 40 with camera image processing in accordance with illustrative embodiments allows auto dose capture and confirmation of correct dose without requiring a wireless exchange between the device(s) 22 and the smartphone 20 and, accordingly, without adding complexity and cost to the injection device(s) 22 such as a pen.

In accordance with a third application (i.e., determination of device or drug failure) of the illustrative embodiments, the medical event image capture app 40 is configured to process captured images to determine if the device 22 or drug is defective. For example, the app 40 can be used to ensure that the patient is drawing up the correct dose by identifying presence of bubbles and informing the patient of the same. Proper aspiration of a dose of medication into a syringe 22 is a critical step that involves the visual detection of any bubbles in the syringe barrel, followed by elimination of the bubbles from the syringe barrel. Oftentimes, users' compromised visual acuity makes it difficult to detect air bubbles. The app 40 advantageously incorporates an image recognition function wherein it can both detect and quantify the volume of air bubbles in a syringe via captured image processing. For example, this processing can be done with 3D image analysis or a typical 2D project surface area image analysis that is traditionally used in counting features in a variety of scientific fields. A 2D image analysis algorithm can be used to quantify the bubble size as well. As described below in connection with FIG. 7C, the app 40 can generate an alert to advise the user that air bubbles can be detected and need to be removed from the syringe barrel prior to delivery. The alert can be visual or audible which is particularly helpful to visually impaired users.

Figure 5:
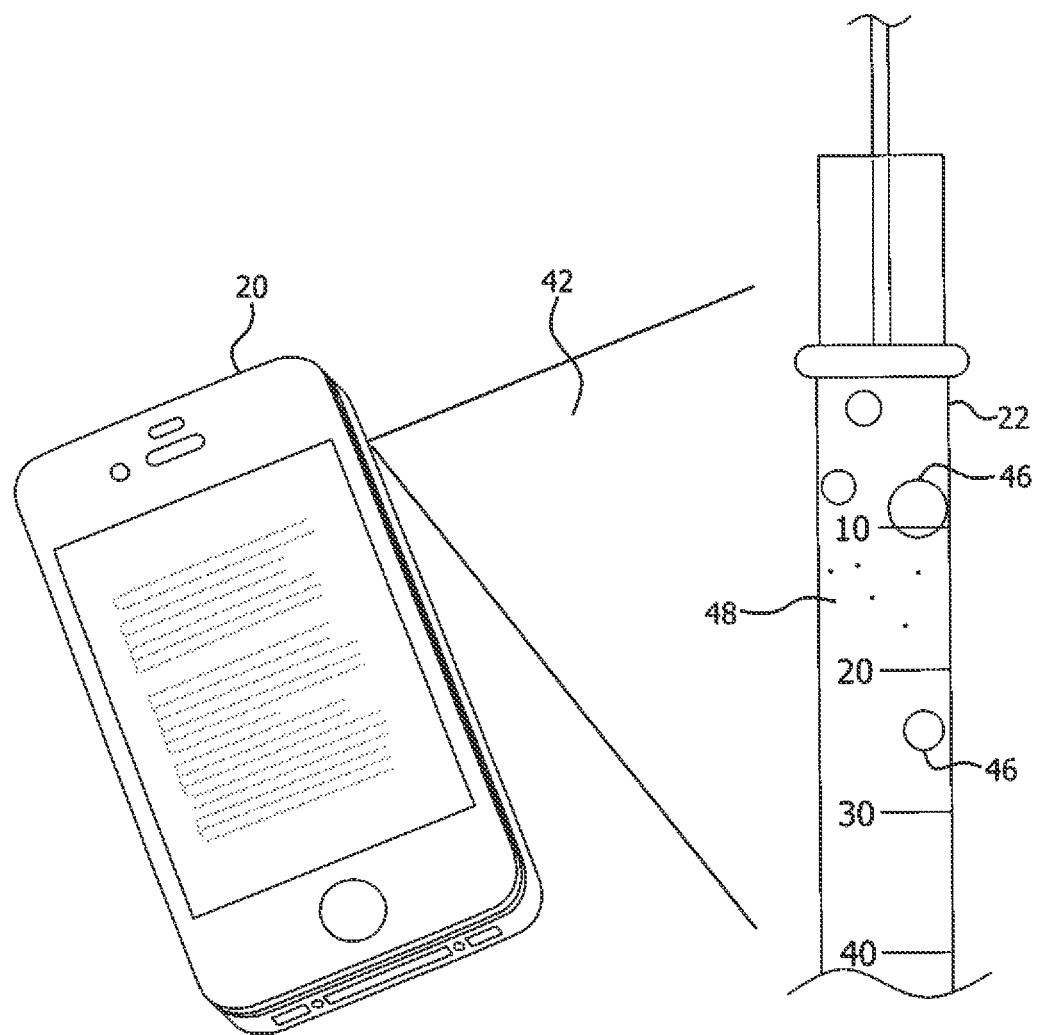

An example is shown in FIG. 5 wherein the projected 2D image/photograph of a syringe 22 with the air bubbles 46 is obtained via the image capture operation of the app 40, and is analyzed by app image processing and analysis software to recognize the shape and size (and hence volume) of the bubbles 46 using the projected surface area in the 2D image. Such image processing can have multiple utilities, such as monitoring the effectiveness of patient use method, providing better teaching or training tools, and potentially even tracking accuracy of dose drawn. The medical event image capture app 40 can also employ captured image processing algorithms that detect other attributes of the item 22 such as determining if particulates 48 are in the medication or the medication is opaque and not sufficiently clear (e.g., signifying that the medication has expired or is contaminated), or if a medical device 22 is missing a safety cap or has a bent or broken needle, among other undesirable attributes. In any event, the app 40 can generate an alert to advise the user that an undesirable attribute of the device 22 or medication has been detected to allow the user an opportunity to resolve the issue before an incorrect dose is delivered.

This third application of the medical event image capture app 40 is particularly beneficial in clinical settings. For example, the smartphone 20 with app 40 can detect visible contamination (e.g., a pen with expired medication indicated as cloudy or having floating particles). The captured image processing algorithm of the app 40 can be configured to detect opaqueness of the medication, for example, or whether a device is leaking. The captured image processing algorithm can also be configured to determine from a captured image of an injection item 22 whether it is missing a safety feature such as a sterilization cap or other needle stick prevention device and generate an alert to the HCP. These safety features may be required by hospital safety procedures and the app 40 can ensure compliance, as well as assist with inventory management and replenishment. For example, the app 40 can detect devices and other supplies used for an injection event for which an image(s) is capture and processed. The processor 26 programmed via the app 40 can advise personal and clinical setting personnel regarding supply levels based on quantity of captured images of used supplies 22 to assist with auto-reordering of supplies. Indeed, many clinical settings provide HCPs with iPhones or mobile devices for alerts and messaging on when to come to the bedside of a patient. The app 40 can be provided to the HCP devices 20 to allow them to capture an image of a medical condition management event and, though processing of the image, gather informatics that assist with auto recording injection data into patients' electronic records, as well as assist clinical setting administration records regarding billing, inventory management and reordering and care plan compliance and clinical effectiveness.

Example image processing algorithms for processing captured images in accordance with illustrative embodiments include, but are not limited to, any of the following image processing and/or image analysis algorithms: image segmentation (e.g., for identification of correct location of boundaries); image representation (e.g., for articulation of an image in the form of pixel maps); detection and recognition (e.g., for recognition of pre-quantified features); motion estimation (e.g., when using dynamic images); tracking (e.g., for tracking of features that have been identified during detection step(s) of illustrative embodiments); surface and shape estimation (e.g., for bubble detection and volume quantification in accordance with illustrative embodiments); enhancement (e.g., for contrast stretching, noise filtering, histogram modification); restoration (e.g., for editing boundaries, aligning contrast, compensating for exposure); analysis (e.g., for identifying, categorizing, and/or counting features); reconstruction; and data compression. Example platforms that support these example image processing and/or image analysis algorithms include, but are not limited to, commercially available platforms such as Matlab, Image J, Icy, ENVI, FIJI, ImageTool, ImagePro Plus, among others, as well as open source platforms.

Figure 6:
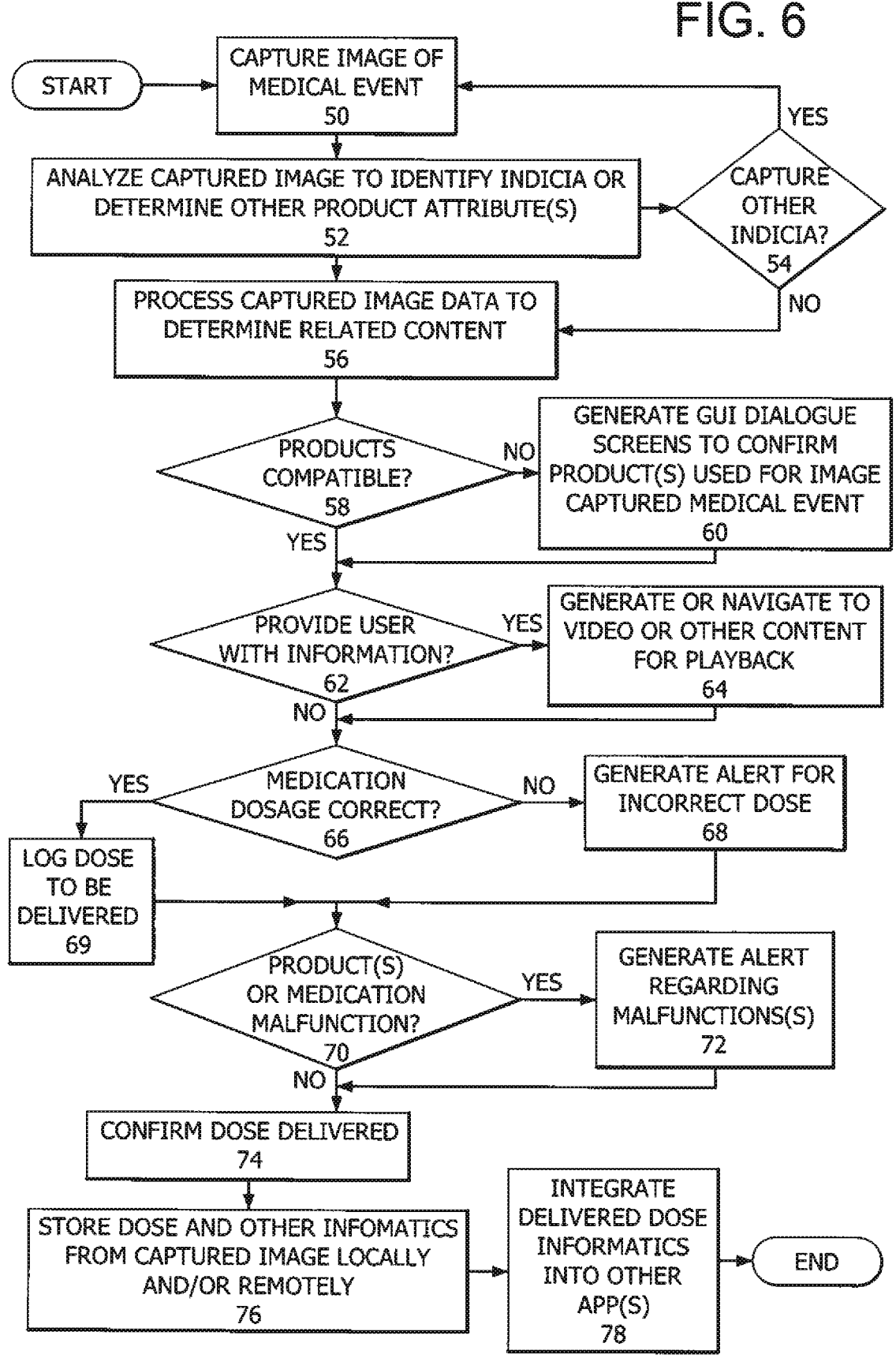
FIG. 6 is a flow chart comprising example operations performed by the device with a medical event image capture app of FIG. 1 in accordance with an illustrative embodiment.

FIG. 6 is a flow chart of example operations of the medical event image capture app 40 in accordance with an illustrated embodiment. It is understood that the app 40 can be provided with all three applications (i.e., (1) correct or compatible device, (2) dose confirmation, and (3) medical device 22 and/or drug malfunction) or any two of these three applications, or only one of these applications. A user uses a smartphone 20 camera 28 function to take an image of devices 22 used to implement a medical management event such as an injection (block 50). The app 40's captured image processing operation determines indicia 24 or, optionally, other attributes of the device(s) 22 (blocks 52 and 54). If indicia 24 or particular attributes are determined to be present from the captured images, the app 40 is configured to control the processor 26 to determine related device information (e.g., table or other data structure stored in a local or remote computer memory device) such as whether medical devices 22 detected in the captured image belong to the same product family or are otherwise compatible, or indicate an amount to be delivered, or indicate a malfunction (block 56). If devices 22 in a captured image are not compatible (e.g., part of different product families as described above), the processor 26 will generate alerts or GUI screens to advise the user of potential incorrect dose due to device 22 incompatibility with drug or other user error in drawing medication or misuse of a medical device 22 (block 60). The indicia 24 detected by the app 40's image processing function can also determine if a QR code or other indicia indicates that the user should receive playback of educational information, as described above (blocks 62 and 64).

With continued reference to FIG. 6, the processor 26 is controlled by the medical event image capture app 40 to determine if the correct dose amount has been drawn and, if not, to generate alerts or GUI screens to the user (block 66 and 68). If the processor 26 detects a device or drug failure, for example, as described in connection with FIG. 5, the processor 26 will generate alerts or GUI screens to advise the user of the problem (blocks 70 and 72). Once the correct dose is confirmed to be delivered (e.g., via a user input on a GUI screen generated by the app 40 on the touchscreen 30) per block 74, the medical event data or informatics (e.g., one or more of confirmed dose, detected malfunction, product 22 codes, among other data obtained via the captured image processing operation of the app 40) can be stored locally or remotely for access and use by the patient and/or other medical condition management stakeholders (block 76). For example, the medical event data or informatics can be automatically uploaded to a repository for inclusion in a patient's electronic record, for medical billing, for auto-replenishment of medical supplies 22, and/or care plan compliance tracking, among other uses such as incorporation into an integrated disease management system as described below in connection with FIG. 10. The app 40 can optionally be used with an injection site rotation algorithm as described in commonly owned U.S. Pat. No. 10,173,015 (block 78). For example, the injection site rotation algorithm can recommend the next body site injection location, and the injection app 40 can capture an image of an injection event and confirm delivered amount to record the injection. The injection site rotation algorithm can also record the body site injection.

Figure 7H:
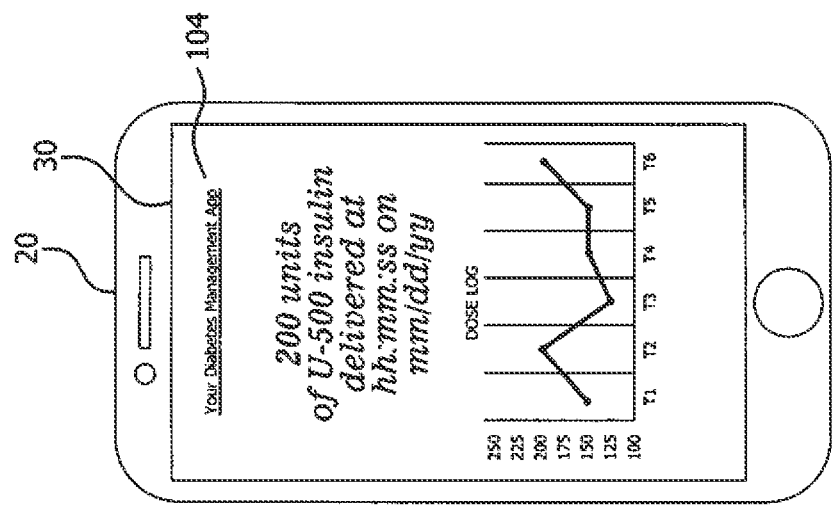
Figure 7G:
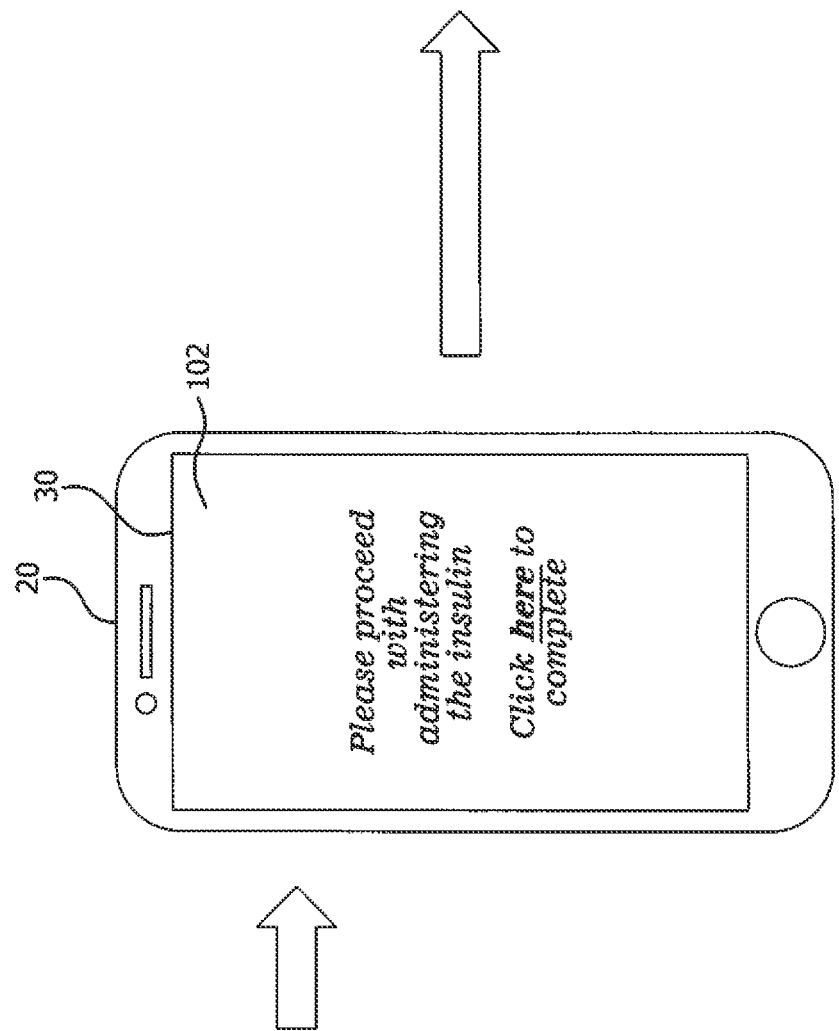
Figure 8E:
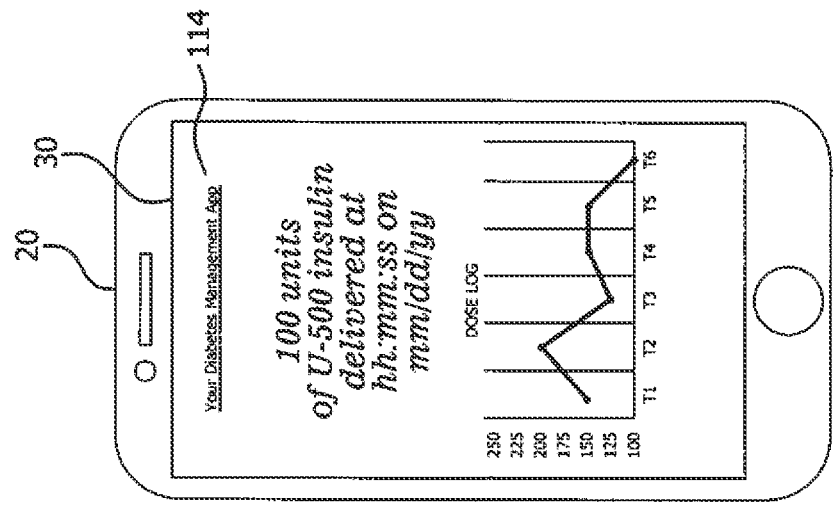
Figure 8D:
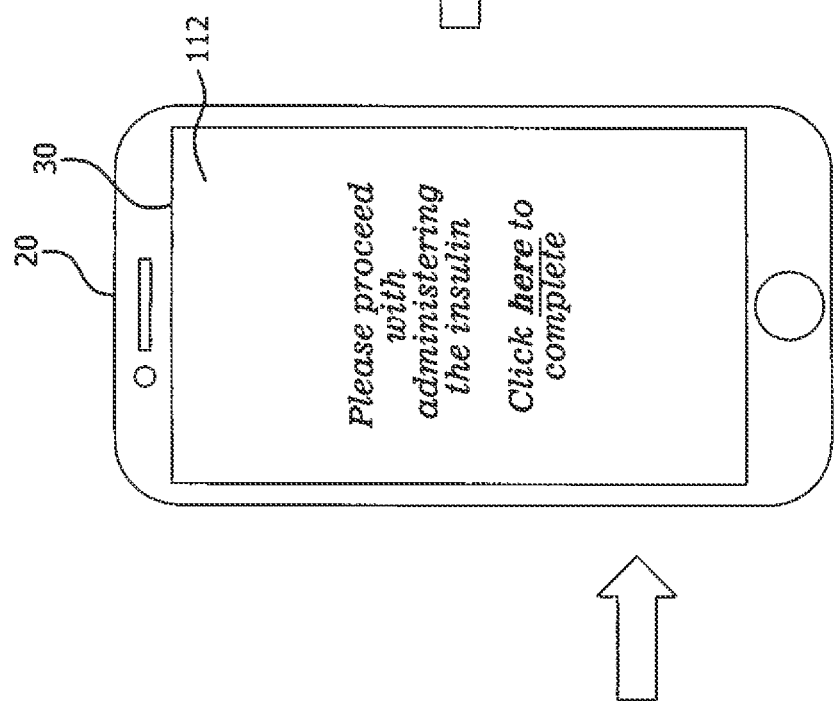

FIGS. 7A, 7B, 7C, 7D, 7E, 7F, 7G and 7H am example GUI screens generated on a device 20 by the medical event image capture app 40 to guide the user to draw a correct dose amount (e.g., with a syringe) and to take an image of a QR code or other indicia 24 on the syringe 22, as depicted in FIG. 7A. The captured image is shown in the screen 92 in FIG. 7B. A user is alerted to the presence of detected air bubbles in the screen 94 in FIG. 7C, which were determined using an image processing algorithm on the captured image. After bubbles are eliminated and a correct medication amount is drawn (FIGS. 7D and 7E), the app 40 generates a screen 100 (FIG. 7F) that requests confirmation that the correct syringe is being used with the type of insulin (e.g., that was detected using indicia 24 in a vial). FIGS. 7G and 7H are confirmation of delivery screens.

Figure 9A:
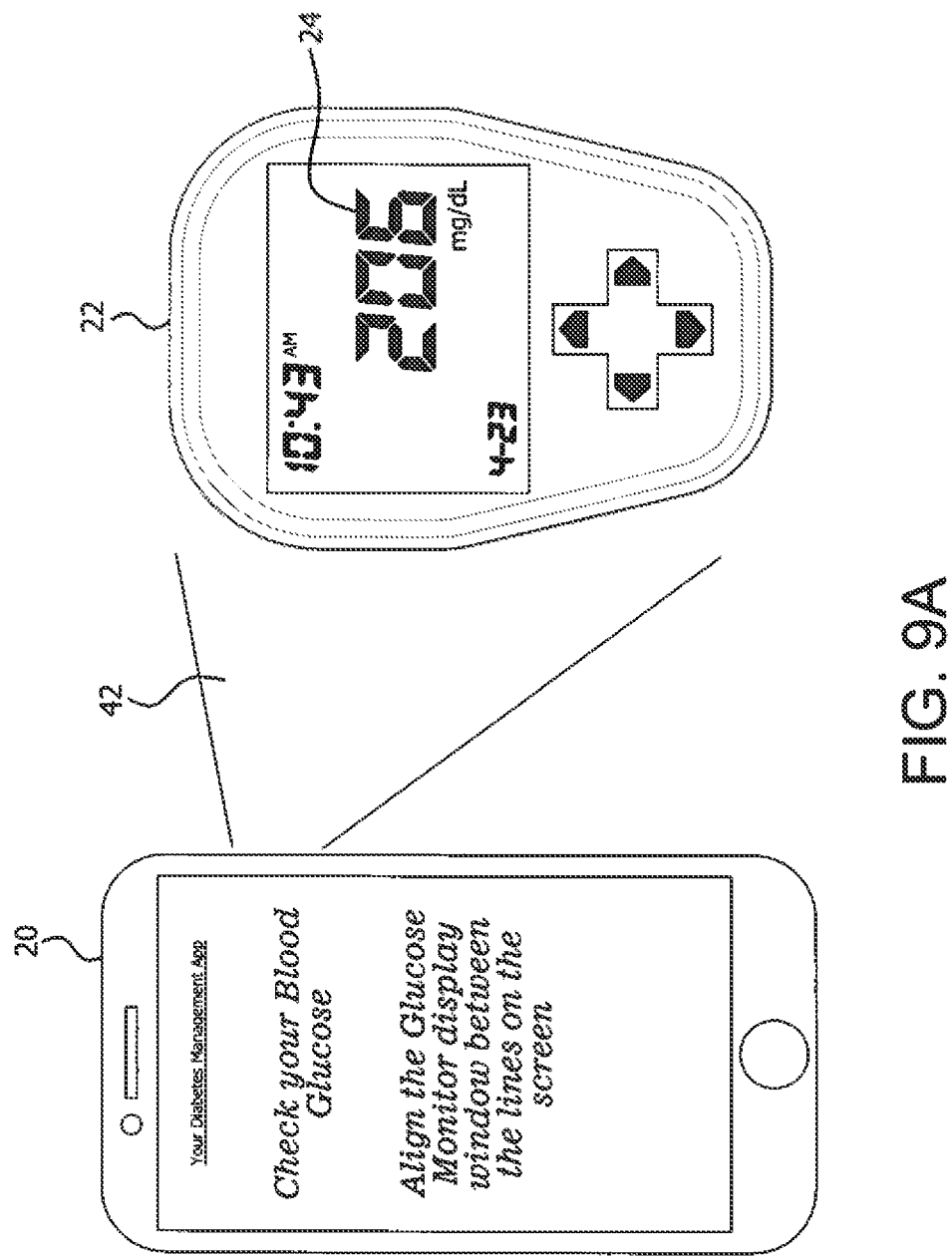
Figure 9C:
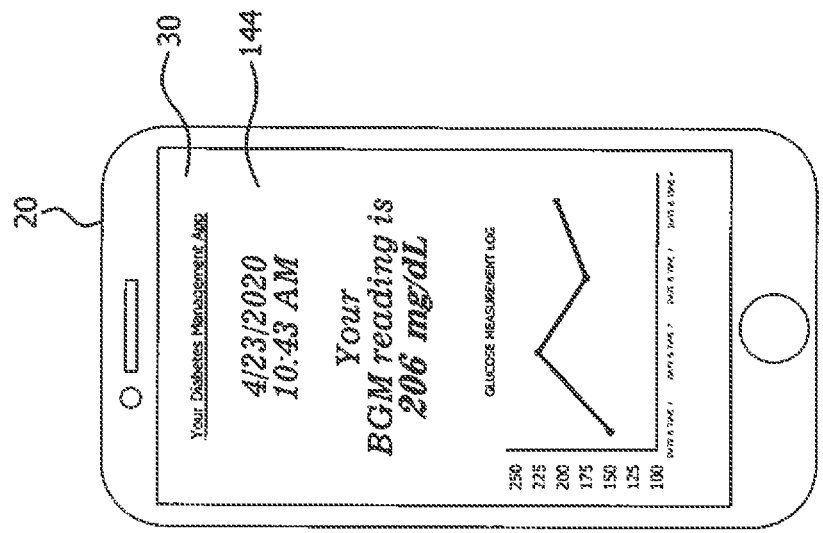
Figure 9B:
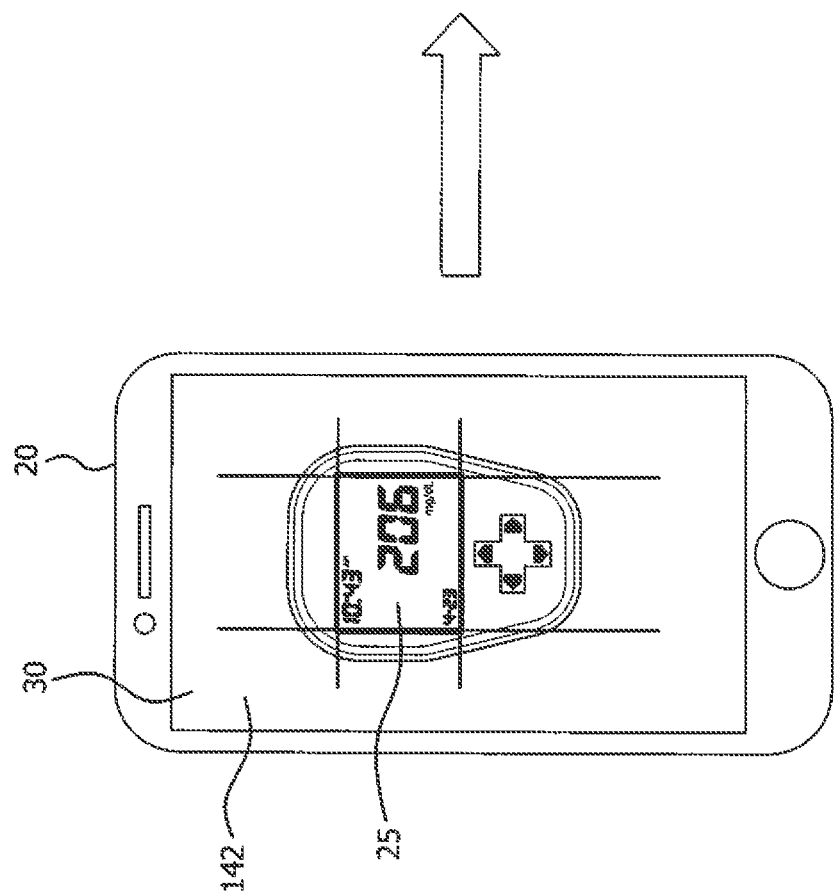

FIGS. 8A, 8B, 8C, 8D and 8E illustrate example GUI screens generated on a device 20 by the app 40 to guide the user in drawing a dose (e.g., with a syringe) wherein no air bubbles are detected, unlike in screens of FIGS. 7B through 7D. In addition to using the app 40 to capture informatics from components such as injection devices or drug vials, the app 40 is also useful to log information from other medical devices such as monitors (e.g., blood glucose monitor (BGM), pulse oximeter, thermometer, blood pressure monitor, among others that may not have a wireless communication interface). FIGS. 9A, 9B and 9C illustrate example GUI screens generated on a device 20 by the app 40 to capture information 24 from a display of a BGM 22 using photo capture as described herein. FIG. 9A shows a device (e.g., smartphone 20) that captures informatics 24 from the display of a BGM 22 within an image range 42 of the smartphone camera 28. The camera image of the informatics 24 (e.g., a glucose reading of 206 mg/dL at 10:43 am is indicated at 25 in FIG. 9B. With reference to FIG. 9C, the app 40 logs the information from the camera image into memory on the smartphone 20 and displays it for the user on the smartphone screen 30. Such passive informatics capture and logging using the app 40 makes devices such as monitors that have no wireless communication interface more versatile and cost effective for some users who do not have affordable access to, for example, a continuous glucose monitoring system that logs glucose readings automatically and wirelessly to another device. The app 40 provides these users with an affordable solution to address known challenges they face with blood glucose tracking and transcription errors by providing an option to electronically log data from their monitor screens that reduces the potential for human error.

Illustrative embodiments disclose multiple ways of better engaging with the user and leveraging the strengths from both the injection products 22 and the medical event image capture app 40 to enhance user experience. The app 40 is used to both identify specific features and activities, confirm they are as intended, provide confirmation to the user and also enable logging and tracking of information for posterity. Overall, the integrated usage of the device(s) 22 and the app 40 are expected to drive better compliance and improved patient outcomes. Additionally, the combination of correct device 22 detection and the monitoring and logging of the delivered dose information is expected to provide more accurate data to enable better clinical decision making and reduce potential for medication errors. While primarily geared towards a self-injecting patient base, the app 40 (and device 22 combination functionality) can just as easily be leveraged in other settings (e.g., institutional and alternate sites) and also by caregivers (e.g., nurses, family members, etc.).

In addition to these various insulin delivery or injection products 22, a diabetes care company can provide a Digital Health (DH) app such as the BD Diabetes Care app, available from Becton Dickinson and Company, that allows patients to maintain improved control on their diabetes treatment regimen. For example, the BD Diabetes Care app assists patients and/or their caregivers with recording injections, recording blood glucose values or glucose monitoring, recording carbohydrates intake, and logging exercise, all of which impact the patient's injected insulin needs.

The medical event image capture app 40 can also be integrated into a digital health app (e.g., BD Diabetes Care app). For example, the medical event image capture app 40 and its generated informatics can be automatically combined with other digital health app content such as logs of injections, exercise, carbohydrates intake and blood glucose readings to assist the patient and disease management stakeholders in tracking a patient's compliance with a prescribed disease management regime (e.g., how well the patient is maintaining target blood glucose levels), reordering supplies (e.g., home health supplies such as self-injection devices and medication, and pharmacy inventory) and auto-shipping of prescribed medications and medical supplies to patients or commercial settings, inventory tracking, billing for medical events captured within clinical settings, and the like. Thus, illustrated embodiments herein provide convenience and other advantages to different categories of users (e.g., self-injection, and caregiver administered injections) in different categories of settings (e.g., in-home setting or other alternate site such as nursing home, long-term care facility and rehabilitation facility, as well as clinical/hospital setting).

The medical event image capture app 40 can be a stand-alone app that communicates with the user (e.g., patient) or other stakeholders on the user's medical condition management team such as caregivers (e.g., parents, spouses, school nurses), health care providers, clinical setting administrators, pharmacies, payers (e.g., insurance companies) and medical device suppliers and distributors.

Figure 10:
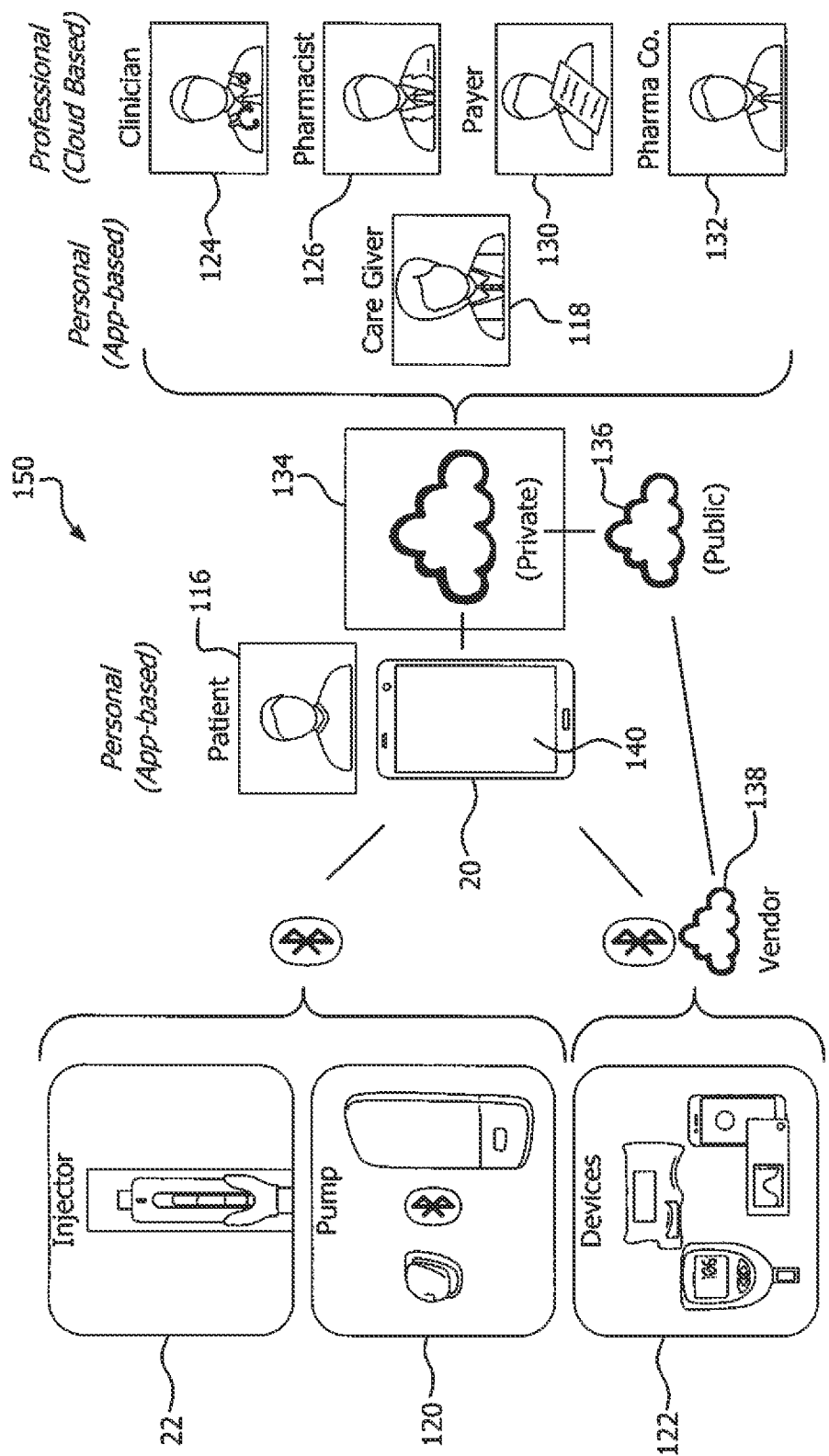
FIG. 10 is an example integrated disease management system using the device with a medical event image capture app of FIG. 1 in accordance with an illustrative embodiment.

The medical event image capture app 40 can also be integrated into an integrated disease management (IDM) system 50 as shown in FIG. 10 in accordance with an illustrative embodiment. The IDM system 150 is understood to be useful to manage other types of diseases involving collection, analysis and dissemination of information to assist disease stakeholders (e.g., patients, care givers, health care providers, disease management companies, pharmacies, disease management-related product suppliers, insurers and other payers) in management of one or more diseases. The IDM system 150 can be used by many types of people, including, but not limited to, diabetic patients, non-diabetic persons, caregivers, and healthcare professionals or healthcare entities such as disease management companies, pharmacies, disease management-related product suppliers, insurers and other payers. For ease of description, this disclosure describes the IDM system with reference to users. Reference to "users" is intended to encompass all types of users, without limit. Further, in some instances, this disclosure refers to patients or diabetic patients. This is done in the context of a non-limiting example, and is not intended to be limiting. Thus, reference to patients or diabetic patients is intended to refer to users of all types, without limit. The IDM system 150 can include an interactive interface that is simple, engaging, and that provides a scalable means for users to seek information and support when needed so that they feel more in control of their condition.

The IDM system 150 can also comprise or have access to a user database and a content database (not shown). For example, healthcare professionals or related organization(s) can develop recommended disease management protocols and recommended lifestyle choices for optimized patient outcomes and store this diabetes information content in the content database. The IDM system 150 is configured to transmit data securely (e.g., encrypted) to a remote server such as a cloud storage server, to perform analysis of received data (e.g., disease management data), to provide feedback to the user (e.g., customized feedback with curated content based on a user's data and interface interactions), and send all or a portion of the data and/or curated content to another user device or remote health management access point (e.g., as cloud storage) where the information can be accessed by healthcare stakeholders, such as the patient's physician or other HCP, family member or other caregiver, pharmacist, disease management company, medical supplier or payer. Conversely, alerts, reminders, and interventions can be provided to the user by the user's network, e.g. an HCP, securely through the IDM system 150.

User access to the IDM system 150 is via a user device 20 with interactive interface that can be accessible via a web browser or a software application (such as an app for a smartphone or a computer application, for example). The user device 20 can be, but is not limited to, a smartphone, smart watch, tablet, laptop, computer, personal digital assistant ("PDA"), and the like. In some instances, the user device 20 is a mobile device, such as any mobile device known in the art, including, but not limited to, a smartphone, a tablet computer, or any telecommunication device with computing ability, a mobile device connection module, and preferably an adaptable user interface such as, but not limited to a touchscreen. A user typically uses such a mobile device for various functions such as sending and receiving phone calls, sending and receiving text messages, and/or browsing the internet. The user device 20 communicates with the IDM system via a wireless network and/or a wired network.

In accordance with an aspect of the illustrated embodiment in FIG. 10, the IDM system operates in conjunction with an IDM personal app 140 installed on a user device 20 operated by a patient and an IDM professional app downloaded or otherwise installed on a user device 20 operated by professionals such as a clinician 124, a pharmacist 126, a payer 130 and a pharmaceutical company 132. The IDM apps (e.g., the IDM personal app 140) can be operated in a cloud-dependent configuration whereby the mobile device with app transfers data to and receives data from a cloud (e.g., the IDM system) during an app session, for example, or periodically or continuously in the background, or can be operated in a distributed configuration whereby the app functions in a standalone mode and then connects as needed to selectively to the cloud (e.g., the IDM system).

For example, the IDM personal app 140 can show as a single icon on a patient's device(s) 20. The IDM personal app 140 provides an interface to the IDM system for a patient or a patient's caregiver for such functions and experiences as viewing dose data, texting with a clinician, adding meal data to the patient's stored data, importing BG data, and so on. The IDM personal app 140 can incorporate the operations of the medical event image capture app 40 to obtain and store informatics from captured images such as dose amount, event date/time stamps associated with the captured images, products 22 identified via captured images, among other data. The IDM professional app provides an interface to the IDM system for other users such as a clinician 124, pharmacist 126, payer 130, pharmaceutical company 132 or other medical company, among others, for such functions as viewing a patient's data or a patient population's data, texting a patient and performing dose titration, among other functions. The IDM personal (patient, caregiver) software 140 can comprise one or more apps, for example. The DM professional (clinicians, pharmacists, etc.) software can be web-based for different user types and provides a separate experience for the patient's care team providers, payers and pharmacists). For example, the IDM professional app can be programmed to bring in data from patients' IDM personal apps 140.

With continued reference to FIG. 10, the user device 20 can be connected to other devices (e.g., via Bluetooth™) such as one or more medication delivery devices (MDDs) 22 (e.g., an insulin injector 22 and/or a pump indicated at 120), and other devices such as glucose or lifestyle monitoring devices indicated generally at 122. For example, the other devices can include, but are not limited to, one or more of a carbohydrate input device or app running on a use's cellphone that allows the patient to input food and drink consumed, a device or related app having an oral medication input element that permits a user to track oral medications ingested, a BGM and/or CGM, and a device or app for inputting wellness data such as user activity level. The IDM personal app 140, once downloaded, allows the user to selectively activate additional functionality such as that associated with respective smart devices such as MDD(s) (e.g., an injection pen 22 app, pump 120 app or other dose capture app). An MDD app can provide device connectivity and data offload functions, and dose data storage and access functions, dose data to cloud transfer functionality, user profile creation and authentication functionality, connected third party experiences (e.g., interaction between the user and a third party such as a vendor for BG data tracking), and output and analysis of dose data and BGM data. With reference to FIG. 10, some device data can be sent to the user device 20 with IDM personal app 140 for storage on private cloud, whereas other data (e.g., non-proprietary or unregulated medical device data from devices) can be transmitted to a public cloud 136 by the devices or their vendor 138 for access by the user devices 20.

Similarly, the IDM professional app can be selectively configured with different functionality by different stakeholders to include, for example, a patient population management sub-app, and a patient outcomes sub-app, and a data and communication protocols application programming interface (API) to enable transmission of data between users and systems. Some examples are a proprietary cloud or "closed API" that allows users to create accounts and gain direct access to data and functionality through app views, a commercial cloud or "open API" wherein data is passed to another entity (e.g. Glooko) to facilitate use by the end-user (e.g., via an open API), or a hybrid model that simultaneously offers both of the above open and closed API options to utilize proprietary data generated from devices with closed APIs as well as data from devices with open APs.

In accordance with an aspect of the embodiment illustrated in FIG. 10, one or more of the devices 22, 120 and 122 are connected devices that can communicate data (e.g., delivered amounts of medication and blood glucose readings) directly to the IDM system. An example of a connected medication delivery device (MDD) is described in commonly owned US20160074587 incorporated by reference herein. A platform for connected device communication with the IDM system is described below. The IDM system and connected devices (e.g., MDDs 12, 120 and other devices 122) advantageously provide an end-to-end IDM solution for people with diabetes (PWD) and their care network (e.g., health care provider(s), caregiver(s), pharmacist and insurance company) to ease the burden of managing diabetes on the PWD as well as on other disease management stakeholders. This IDM solution transforms data to bring enhanced end user experiences for improved outcomes. This IDM solution can be implemented as a collection of products that broadly address needs associated with a specific medical condition such as diabetes, although the IDM solution can be configured to manage different medical conditions. The products can be hardware and/or software that deliver value to a defined group of people such as patients or caregivers, or professional disease management personnel such as health care provider, pharmacist and insurance company. The software products described herein (e.g., phone apps or computer applications) can comprise one or more modules, a module being understood to be collection of functionalities that delivers a set of experiences such as discreet events, tasks, and actions, for example.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the illustrative embodiments can be easily construed as within the scope of claims exemplified by the illustrative embodiments by programmers skilled in the art to which the illustrative embodiments pertain. Method steps associated with the illustrative embodiments can be performed by one or more programmable processors executing a computer program, code or instructions to perform functions (e.g., by operating on input data and/or generating an output). Method steps can also be performed by, and apparatus of the illustrative embodiments can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of claims exemplified by the illustrative embodiments. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

Computer-readable non-transitory media includes all types of computer readable media, including magnetic storage media, optical storage media, flash media and solid state storage media. It should be understood that software can be installed in and sold with a central processing unit (CPU) device. Alternatively, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. A portable device for capturing images of medical events to reduce medical errors, comprising:
   an imaging device for imaging at least one medical product in use during a medical event;
   a memory to store images captured by the imaging device and program instructions for processing captured images;
   a user interface configured to generate an output to a user; and
   a processor adapted to execute the program instructions to
       analyze a captured image associated with the medical event to detect a characteristic of the medical product selected from the group consisting of an indicia on the medical product, and a designated attribute of the medical product,
       analyze the detected characteristic to determine when a medical error occurs, the medical error corresponding to when the medical product is incompatible with the medical event, mishandled by the user, or malfunctioning, and
       generate an output to the user via the user interface comprising an alert related to the medical error;
   wherein at least one captured image in the memory corresponds to a medical event involving at least two medical products used together; and
   wherein the processor is configured to
       analyze the at least one captured image to detect indicia on each of the at least two medical products,
       analyze the indicia on each of the at least two medical products using previously stored medical product data that is locally or remotely accessible by the processor, the previously stored medical product data comprising indicia for respective ones of a plurality of different medical products and, for each medical product among the plurality of different medical products, the corresponding indicia of one or more other medical products indicated as compatible with that medical product, and generate an output to the user when the processor determines that the at least two medical products are incompatible according to the previously stored medical product data.

2. A portable device for capturing images of medical events to reduce medical errors, comprising:

an imaging device for imaging at least one medical product in use during a medical event a memory to store images captured by the imaging device and program instructions for processing captured images;

a user interface configured to generate an output to a user; and a processor adapted to execute the program instructions to analyze a captured image associated with the medical event to detect a characteristic of the medical product selected from the group consisting of an indicia on the medical product, and a designated attribute of the medical product, analyze the detected characteristic to determine when a medical error occurs, the medical error corresponding to when the medical product is incompatible with the medical event, mishandled by the user, or malfunctioning, and generate an output to the user via the user interface comprising an alert related to the medical;

wherein the medical device is a medication delivery device having indicia; and wherein the processor is configured to analyze a captured image of the medication delivery device and detect the indicia, analyze the or other captured image of the medication delivery device medication and detect an amount of medication indicated for delivery by the medication delivery device, using previously stored medical product data that is locally or remotely accessible by the processor, the previously stored medical product data comprising a plurality of different medication delivery devices and their respective indicia and, for each medication delivery device among the plurality of different medication delivery devices, specifications for designated amounts of medication that can be delivered via that medication delivery device, determine the designated amount of medication corresponding to the medication delivery device associated with the indicia detected from the captured image, and generate an alert via the user interface when the detected amount of medication indicated for delivery is determined to be different from the designated amount of medication.

3. The portable device as claimed in claim 2, wherein the detected amount of medication indicated for delivery corresponds to a marking in the captured image that is associated with at least one of a dose input on an injection pen, and a level indicator on a syringe barrel that is adjacent to fluid level in the syringe.

4. The portable device as claimed in claim 2, wherein the processor uses an algorithm chosen from a two-dimensional image processing algorithm and a three-dimensional image processing algorithm to analyze the or other captured image and detect the amount of medication indicated for delivery by the medication delivery device.

5. The portable device as claimed in claim 2, wherein the processor is configured to generate an alert via the user interface when a prescribed amount of medication indicated for delivery is determined to be different from the designated amount of medication.

6. The portable device as claimed in claim 5, wherein the processor is configured to analyze the or other captured image of the medication delivery device medication and detect an amount of medication indicated for delivery by the medication delivery device, the detected amount of medication indicated for delivery corresponding to a marking in the captured image that is associated with a dose input on an injection pen and/or a level indicator on a syringe barrel that is adjacent to fluid level in the syringe, and generate an alert via the user interface when the prescribed amount of medication indicated for delivery is determined to be different from the detected amount of medication indicated for delivery.

7. The portable device as claimed in claim 2, wherein the detected amount of medication indicated for delivery corresponds to a marking in the captured image that is associated with at least one of a dose input on an injection pen and a level indicator on a syringe barrel that is adjacent to fluid level in the syringe.

8. The portable device as claimed in claim 1, wherein the program instructions comprise an algorithm chosen from a two-dimensional image processing algorithm and a three-dimensional image processing algorithm used by the processor to analyze the captured image.

9. A portable device for capturing images of medical events to reduce medical errors, comprising:

an imaging device for imaging at least one medical product in use during a medical event;

a memory to store images captured by the imaging device and program instructions for processing captured images;

a user interface configured to generate an output to a user; and a processor adapted to execute the program instructions to analyze a captured image associated with the medical event to detect a characteristic of the medical product selected from the group consisting of an indicia on the medical product, and a designated attribute of the medical product, analyze the detected characteristic to determine when a medical error occurs, the medical error corresponding to when the medical product is incompatible with the medical event, mishandled by the user, or malfunctioning, and generate an output to the user via the user interface comprising an alert related to the medical;

wherein the processor is configured to analyze at least one captured image to detect a characteristic of the medical product comprising at least one designated attribute of the medical product selected from the group consisting of selected color of medical product, selected dimension of medical product, selected form factor of medical product, presence of safety mechanism on medical product, absence of safety mechanism on medical product as compared with stored image of medical product having safety mechanism, and analyze the detected characteristic to determine whether a medical error has occurred using previously stored medical product data that is locally or remotely accessible by the processor, the previously stored medical product data comprising designated specifications for image characteristics of the medical product corresponding to the at least one designated attribute.

10. The portable device as claimed in claim 9,
wherein the medical product is a liquid medication drawn into a syringe, and the at least one designated attribute of the liquid medication is selected from the group consisting of opaqueness of the liquid medication, presence of bubbles in the liquid medication, presence of particulates in the liquid medication; and
wherein the previously stored medical product data comprises designated specifications for image characteristics of the at least one designated attribute of the liquid medication.

11. The portable device as claimed in claim 2, wherein
the portable device is a mobile phone or a computing device with wireless communications interface,
the memory is configured to store an integrated disease management (IDM) app, the IDM app comprising an IDM personal app operated by a user who is a patient and/or an IDM professional app operated by a healthcare professional, and
the processor is further adapted to execute instructions in accordance with the IDM app to operate the portable device in a cloud configuration with a remote IDM system whereby the IDM app transfers data to and receives data from the IDM system during an app session.

12. The portable device as claimed in claim 11, wherein the portable device operates in accordance with the IDM personal app to transfer to and store informatics from the captured images at the IDM system, the informatics selected from the group consisting of dose amount determined from at least one of the captured images, medical event date and/or time stamps determined from at least one of the captured images, and medical products identified from at least one of the captured images.

13. The portable device as claimed in claim 12, wherein the portable device operates in accordance with the IDM professional app to determine patient information from the informatics stored in the IDM system, the patient information comprising compliance data for a prescribed regimen based on the informatics related to dose amount and medical event date and/or times, medical product prescription renewal data based on the informatics related to the medical products identified from the captured images and medical event date and/or times corresponding to use of these medical products, and/or billing data corresponding to medical products identified from the captured images and medical event date and/or times corresponding to use of these medical products.

14. The portable device as claimed in claim 13, wherein the portable device can be connected wirelessly to at least one other medical condition management device and obtain medical event information therefrom, the processor is further adapted to execute instructions in accordance with the IDM app to transfer the medical event information to the IDM system.

15. The portable device as claimed in claim 11, wherein the cloud configuration comprises a private cloud and a public cloud, and the portable device operates in accordance with the IDM app to determine whether at least one of the informatics and other data related to the user that is stored in the memory is proprietary data or non-proprietary data and to selectively transfer the proprietary data via the private cloud and the non-proprietary data via the public cloud.

16. A portable device for capturing images of medical events comprising:
an imaging device for imaging at least one medical product in use during a medical event;
a memory to store images captured by the imaging device and program instructions for processing captured images;
a user interface configured to generate an output to a user; and
a processor adapted to execute the program instructions to
analyze a captured image associated with the medical event to detect a characteristic of the medical product selected from the group consisting of an indicia on the medical product, and a designated attribute of the medical product,
store data related to the detected characteristic in the memory, and
generate an output to the user via the user interface using the data related to the detected characteristic;
wherein the portable device is a monitor for a selected medical condition, and the detected characteristic is a monitored parameter detected by the monitor and indicated via a user output interface associated with the monitor.

17. The portable device as claimed in claim 16, wherein the processing is adapted to execute the program instructions to log a date and/or time associated with the detected characteristic.

18. The portable device as claimed in claim 16, wherein the monitor is selected from the group consisting of a pulse oximeter, thermometer, blood pressure monitor, and blood glucose monitor.

19. The portable device as claimed in claim 1, wherein each of the at least two medical products are chosen from injection pens, injection pen needle assemblies, syringes, and syringe safety injection products, surgical instruments, blood collection and delivery products, medications.

20. The portable device as claimed in claim 2, wherein the program instructions comprise an algorithm chosen from a two-dimensional image processing algorithm and a three-dimensional image processing algorithm used by the processor to analyze the captured image.

* * * * *